United States Patent
Ryncarz

(10) Patent No.: US 7,070,962 B1
(45) Date of Patent: Jul. 4, 2006

(54) POSITIVE CONTROLS IN POLYNUCLEOTIDE AMPLIFICATION

(75) Inventor: Alexander J. Ryncarz, Santa Fe, NM (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 08/791,240

(22) Filed: Jan. 30, 1997

Related U.S. Application Data

(60) Provisional application No. 60/010,948, filed on Feb. 1, 1996.

(51) Int. Cl.
*C12Q 1/68* (2006.01)
*C12P 19/34* (2006.01)
*C12N 9/98* (2006.01)
*C07H 21/04* (2006.01)
*C07H 21/00* (2006.01)

(52) U.S. Cl. .................. 435/91.2; 435/6; 435/91.1; 435/187; 536/23.1; 536/24.33; 536/25.3

(58) Field of Classification Search .............. 435/6, 435/91.1, 91.2, 183; 536/23.1, 24.3, 24.33; 935/76, 77
See application file for complete search history.

(56) References Cited

U.S. PATENT DOCUMENTS

| | | | | |
|---|---|---|---|---|
| 4,683,202 | A * | 7/1987 | Mullis | 435/91 |
| 5,391,480 | A * | 2/1995 | Davis et al. | 435/6 |
| 5,427,932 | A * | 6/1995 | Weier et al. | 435/91.2 |
| 5,436,149 | A * | 7/1995 | Barnes | 435/194 |
| 5,491,086 | A * | 2/1996 | Gelfand et al. | 435/194 |
| 5,491,133 | A | 2/1996 | Walder et al. | |
| 5,556,772 | A * | 9/1996 | Sorge et al. | 435/91.2 |
| 5,618,664 | A * | 4/1997 | Kiessling | 435/2 |
| 5,627,054 | A * | 5/1997 | Gillespie | 435/91.2 |
| 6,482,590 | B1 * | 11/2002 | Ullman et al. | 435/6 |

FOREIGN PATENT DOCUMENTS

| | | |
|---|---|---|
| WO | WO 93/22456 A1 * | 11/1993 |
| WO | 94/04706 | 3/1994 |
| WO | 96/41000 | 12/1996 |

OTHER PUBLICATIONS

Sommer and Tautz, Minimal homology requirements for PCR primers, Nucleic Acids Research, vol. 17, No. 16, 1989, p. 6749.*
S. Diviacco, et al. "A Novel Procedure For Quantitative Polymerase Chain Reaction By Complification Of Competitive Templates", GENE, vol. 122, No. 2, Jan. 1, 1992, pp. 313-320.
A.M. Wang, et al. "Quantitation Of mRNA By The Polymerase Chain Reaction", Proceedings Of The National Academy Of Sciences Of USA, vol. 86, No. 24, Dec. 1, 1989, pp. 9717-9721.
A. Skerra, "Phosphorothioate Primers Improve The Amplification Of DNA Sequences By DNA Polymerases With Proofreading Activity", Nucleic Acids Research, vol. 20, Jul. 25, 1992, No. 14, pp. 3551-3554.
Int'l Search Report dated Aug. 8, 1997 re Int'l Appln. No. PCT/IB97/00226.

* cited by examiner

*Primary Examiner*—Bradley L. Sisson
(74) *Attorney, Agent, or Firm*—William C. Coppola

(57) ABSTRACT

The present invention relates to an improvement in a method for amplifying a target sequence of a target polynucleotide. The method comprises the step of forming extension products of an oligonucleotide primer at least along the target sequence or along an extended oligonucleotide primer. The extension products are copies of the target sequence. The improvement comprises forming the extension products in the presence of a second polynucleotide, to which the oligonucleotide primer hybridizes except for 1–10 nucleotides at the 3'-end of the oligonucleotide primer. Under the conditions chosen, the oligonucleotide primer is extended along the second polynucleotide in a controlled manner relative to extension of such primer along the target sequence, thus providing a positive control for the amplification reaction, which control may be qualitative or quantitative. Optionally, a modified oligonucleotide primer is included in the amplification reaction. The modified primer is substantially identical to the oligonucleotide primer with the exception of a chemical modification at its 3'-end that prevents degradation, under the reaction conditions, of the 1–10 nucleotides referred to above. The method finds particular application in the area of nucleic acid amplification.

58 Claims, 4 Drawing Sheets

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

CGACTCACTA TAGGGCGAAT TGGGC    25

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ix) FEATURE: N at position 25 is guanine phosphorothioate.
               N at position 26 is cytosine phosphorothioate.

-continued (xi) SEQUENCE DESCRIPTION: SEQ ID NO:2:

CGACTCACTA TAGGGCCGAA TTGGNN                26

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:3:

CATTAGGCAC CCCAGGCTTT ACAC                  24

POSITIVE CONTROLS IN POLYNUCLEOTIDE AMPLIFICATION

CROSS-REFERENCE TO RELATED APPLICATIONS

The present application is a continuation of U.S. Provisional Application Serial No. 60/010,948 filed on Feb. 1, 1996; the disclosure of which is fully incorporated herein by reference.

BACKGROUND OF THE INVENTION

1. Field of the Invention

Significant morbidity and mortality are associated with infectious diseases. More rapid and accurate diagnostic methods are required for better monitoring and treatment of disease. Molecular methods using DNA probes, nucleic acid hybridizations and in vitro amplification techniques are promising methods offering advantages to conventional methods used for patient diagnoses.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labeling of DNA with T4 polynucleotide kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

One method for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labeled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, such a method is slow and labor intensive, and nonisotopic labels that are less readily detected than radiolabels are frequently not suitable.

A method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

Another method has also been described for amplifying nucleic acid sequences. This method is referred to as single primer amplification. The method provides for the amplification of a target sequence that possesses a stem-loop or inverted repeat structure where the target sequence is flanked by relatively short complementary sequences. Various methods for creating such a target sequence in relation to the presence of a polynucleotide analyte to be detected have also been described.

The above methods are extremely powerful techniques for high sensitivity detection of target DNA molecules present in very small amounts. The correlation between the number of original target DNA molecules and the number of specifically amplified products is influenced by a number of variables. Minor variations in buffer or temperature conditions can greatly influence reaction-to-reaction amplification efficiencies. Further, clinical samples of DNA targets can contain inhibitory factors that can suppress enzymatic amplification.

When amplifying a target sequence of a nucleic acid for use in clinical diagnostics, there is a need to assure that each amplification reaction is capable of yielding an amplified product. In particular, commercial diagnostic products require validation measures to avoid misdiagnosis due to improper assay methods or contaminated or inactive reagents. Of importance is the development of an internal positive control for demonstrating that the reagents and the detection methodology are working properly. Without such a control the failure of an assay to show the presence of a target nucleic acid sequence may be due to the absence of the target or may be caused by a failure of one or more reagents or of an instrument used in conducting an assay.

Various approaches have been developed for qualification or quantitation of amplification reactions and these approaches can be divided into two main categories, namely, homologous controls and heterologous controls. Such controls have been applied to amplification of mRNA and adapted for DNA analytes. Heterologous controls have a control polynucleotide that does not contain target sequences. One such approach is known as the "endogenous standard" assay, which utilizes as a standard an endogenous polynucleotide that is expressed at a relatively constant level in all samples to be tested. The level of the test sequence is then compared to the standard. Heterologous controls are commonly amplified regions of human DNA such as HLA-DQ and beta-globin genes or mRNA. Heterologous controls assure the adequacy of all the non-target specific reagents and the procedure but are insensitive to any problem involving a target-specific reagent.

Homologous controls utilize a control polynucleotide that contains some of the same sequences as the intended target, but is distinguishable from the target by a difference in size or by the presence or absence of a unique sequence such as a restriction site. Homologous controls contain exogenous nucleic acid fragments, i.e., they are not naturally present in a sample, and they are constructed so that they can be amplified with the same primers used to amplify the target. In this approach a synthetic standard is designed to have only slight variations in sequence but readily distinguishable from a target sequence. The sample to be assayed and the synthetic standard are amplified in the same reaction vessel and any variable that may affect amplification should affect both the target and the control equally.

Generally, in the above methods there is a competition between amplification of the control and the target if present, such as competing for binding to primers and for the other reagents such as deoxynucleoside triphosphates and polymerase. The competition results usually because of the availability of only a limited amount of the polymerase. As a result the presence of a high concentration of one of these species can block amplification of the other and thus potentially interfere with detection of either the control or the target. Thus, for example, in order to achieve co-amplification of two DNA species of similar size in PCR, it is usually necessary to begin the amplification with nearly equal concentrations of the two DNA target sequences.

2. Description of the Related Art

U.S. Pat. No. 5,219,727 (Wang, et al.) discusses a method for determining the amount of a target nucleic acid segment in a sample by polymerase chain reaction. The method involves the simultaneous amplification of the target nucleic acid segment and an internal standard nucleic acid segment. The amount of amplified DNA from each segment is determined and compared to standard curves to determine the amount of the target nucleic acid segment present in the sample prior to amplification. The method has particular applicability for determining the quantity of a specific mRNA species in a biological sample. This development is also discussed by Wang, et al. in *Proc. Nat. Acad. Sci. USA* (1989) 86:9717–9721.

Quantitative PCR methods are disclosed by Eeles, et al. in "Polymerase Chain Reaction (PCR): The Technique and Its Applications" (1993) Chapter 6, pages 55–61, R.G. Landes Company.

The elimination of false negatives in nucleic acid amplification is discussed in European Patent Application No. WO 94/04706 (Kievits, et al.). Prior to amplification an internal control is added to the sample. The control has a nucleic acid distinguishable from the analyte nucleic acid that can be amplified with the same amplification reagents as the analyte nucleic acid, preferably a nucleic acid sequence corresponding to the analyte nucleic acid that has been mutated to discriminate it from the analyte nucleic acid.

Celi, et al., describe a rapid and versatile method to synthesize internal standards for competitive PCR in *Nucleic Acids Research* (1993) 21(4):1047.

Gilliland, et al., discuss the analysis of cytokine mRNA and DNA: detection and quantitation by competitive polymerase chain reaction in *Proc. Natl. Acad. Sci. USA* (1990) 87:2725–2729.

PCR mimics:competitive DNA fragments for use as internal standards in quantitative PCR are disclosed by Siebert, et al., in *Biotechniques* (1993) 14(2):244–249.

Piatak, et al., describe quantitative competitive polymerase chain reaction for accurate quantitation of HIV DNA and RNA species in *Biotechniques* (1993) 14(1):70–80.

Quantitative PCR and RT-PCR in virology is disclosed by Clementi, et al., in *PCR methods and Applications* (1993) 2:191–196.

Competitive polymerase chain reaction using an internal standard: application to the quantitation of viral DNA is discussed by Telenti, et al., *Journal of Virological Methods* (1992) 39:259–268.

Eckstein, et al., *TIBS* (1989) 14:97–100 describes phosphorothioates in molecular biology.

Ott, e al., *Biochemistry* (1987) 26:8237–8241 discloses protection of oligonucleotide primers against degradation by DNA polymerase I.

A process for amplifying, detecting and/or cloning nucleic acid sequences is disclosed in U.S. Pat. Nos. 4,683,195, 4,683,202, 4,800,159, 4,965,188 and 5,008,182. Sequence polymerization by polymerase chain reaction is described by Saiki, et al., (1986) *Science*, 230: 1350–1354. Primer-directed enzymatic amplification of DNA with a thermostable DNA polymerase is described by Saiki, e al., *Science* (1988) 239:487.

U.S. patent application Ser. Nos. 07/299,282 (abandoned) and 07/399,795, filed Jan. 19, 1989, and Aug. 29, 1989, respectively, describe nucleic acid amplification using a single polynucleotide primer (ASPP). U.S. patent application Ser. No. 07/555,323 filed Jul. 19, 1990 (now U.S. Pat. No. 5,595,891), discloses methods for producing a polynucleotide for use in single primer amplification. U.S. patent application Ser. No. 07/555,968 now U.S. Pat. No. 5,439,793), describes a method for producing a molecule containing an intramolecular base-pair structure. A method for producing a polynucleotide for use in single primer amplification is described in U.S. patent application Ser. No. 07/776,538 (abandoned) filed Oct. 11, 1991. The disclosures of these five applications are incorporated herein by reference including the references listed in the sections entitled "Description of the Related Art."

Amplification of nucleic acid sequences using oligonucleotides of random sequence as primers is described in U.S. Pat. No. 5,043,272. A single stranded self-hybridizing nucleic acid probe capable of repeatedly hybridizing to itself or other nucleic acids to form an amplified entity is described in U.S. Patent application Ser. No. 888,058, filed Jul. 22, 1986.

SUMMARY OF THE INVENTION

In its broadest aspect the present invention permits comparison of the amplification of two or more distinct polynucleotides with respect to their relative detectability during the course of the amplification. In accordance with the present invention the amplification of one polynucleotide can be controlled relative to the amplification of another polynucleotide by limiting the amplification of one while allowing the amplification of the other to proceed. This is accomplished by using a single primer for amplification of both polynucleotides where the primer has a 3'-mismatch with respect to its binding site on one of the polynucleotides. The 3'-mismatch permits the regulation of amplification of one of the polynucleotides relative to the other. The amount and timing of such regulation is a direct reflection of the concentration of the polynucleotide that does not have a mismatched priming site. Accordingly, the present method provides for a qualitative or a quantitative determination or control.

One embodiment of the present invention relates to a method for forming multiple copies of a target sequence of a target polynucleotide. The method comprises the step of forming extension products of an oligonucleotide primer at least along the target sequence or along an extended oligonucleotide primer. The extension products are copies of the target sequence. The improvement of the present invention comprises forming the extension products in the presence of a second polynucleotide to which the oligonucleotide primer hybridizes except for the 3'-end of such primer. Under the conditions of the method the oligonucleotide primer is extended along the second polynucleotide in a controlled manner in relation to extension of the oligonucleotide primer along the target sequence. The reaction mixture is examined for the extension products that are copies of the second polynucleotide, the presence of which indicates that the conditions and reagents for amplification of the target sequence are functioning properly. The presence of extension products that are copies of the target sequence is also examined, the presence thereof indicating the presence of the target sequence and the amount thereof, under appropriate control of the amount of such second polynucleotide, indicating the amount of the target sequence.

Another aspect of the present invention relates to an improvement in a method for amplifying a target sequence of a target polynucleotide. The method comprises combining a sample suspected of containing the target polynucleotide with reagents for amplifying the target sequence if present and subjecting the combination to conditions wherein the target sequence if present is amplified. The reagents comprise an oligonucleotide primer and a polymerase. The present improvement comprises including in the combination a control polynucleotide to which the oligonucleotide primer hybridizes except for 1–10 nucleotides at the 3'-end of the oligonucleotide primer. Also included in the combination is a 3' to 5' exonuclease when the polymerase does not have, under the conditions of amplification reaction, 3' to 5' exonuclease activity. The oligonucleotide primer extends along the target sequence. Other molecules of the oligonucleotide primer extend along the control polynucleotide only after the 1–10 nucleotides are degraded by the 3' to 5' exonuclease activity. The reaction mixture is examined for copies of the control polynucleotide, the presence thereof indicating that the reagents and conditions for amplifying the target sequence are functional. Optionally, a modified oligonucleotide primer is included in the above combination. The modified primer is substantially identical to the oligonucleotide primer with the exception of a chemical modification at its 3'-end that prevents degradation by the 3' to 5' exonuclease activity, under the reaction conditions, of the 1–10 nucleotides referred to above.

Another embodiment of the present invention is an improvement in a method for forming multiple copies of a target sequence of a single stranded target polynucleotide ("target sequence"). In the method a first polynucleotide primer ("first primer") is hybridized to the 3'-end of the target sequence. The first primer is extended in the presence of a polymerase along at least the target sequence and is capable of hybridizing to, and being extended along, (1) the extended first primer or (2) an extended second polynucleotide primer ("second primer"). The extended second primer results from the extension of a second primer capable of hybridizing to and extending along a polynucleotide that is complementary (complementary polynucleotide) to the target sequence. The extended first primer is dissociated from the target sequence. The first or the second primer is hybridized to the 3'-end of the extended first primer. The first or said second primer is extended along the extended first primer. The extended first primer or the extended second primer is dissociated from the extended first primer. The first primer is hybridized to the 3'-end of the extended first or second primer. The latter three steps are then repeated. The present improvement comprises including, in the same reaction mixture subjected to the above steps, a control polynucleotide to which the oligonucleotide primer hybridizes except for 1–10 nucleotides at the 3'-end of the primer. Also included in the combination is a 3' to 5' exonuclease when the polymerase does not comprise a 3' to 5' exonuclease. The oligonucleotide primer extends along the target sequence and the second primer extends along the complementary polynucleotide. In addition, the first or the second primer extends along the control polynucleotide only after the 1–10 nucleotides are degraded by the 3' to 5' exonuclease activity of the polymerase. Optionally, a modified oligonucleotide primer is included in the above combination. The modified primer is substantially identical to the oligonucleotide primer with the exception of a chemical modification at its 3'-end that prevents degradation, under the reaction conditions, of the 1–10 nucleotides referred to above.

Another embodiment of the present invention is directed to a method for forming multiple copies of at least one double stranded polynucleotide ("polynucleotide"), where the polynucleotide comprises a single stranded target polynucleotide sequence ("target sequence") and its complementary sequence. The method has a positive internal control. In the method a sample suspected of containing one or more of the double stranded polynucleotides is treated with oligonucleotide primers capable of hybridizing to a portion of each target sequence and its complementary sequence suspected of being present in the sample under conditions for hybridizing the primers to, and extending the primers along, the target sequence and the complementary sequences. The primers are selected such that the extension product formed from one primer, when it is dissociated from its complement, can serve as a template for the formation of the extension product of another primer. Also included in the above are a 3' to 5' exonuclease and a control polynucleotide as a template to which at least one of the primers hybridizes except for 1–10 nucleotides at the 3'-end of the primer. The primers extend, respectively, along the target sequence and the complementary sequence and one of the primers extends along the control polynucleotide only after the 1–10 nucleotides are degraded by the 3' to 5' exonuclease. Optionally, a modified oligonucleotide primer is included in the above combination. The modified primer is substantially identical to the oligonucleotide primer with the exception of a chemical modification at its 3'-end that prevents degradation, under the reaction conditions, of the 1–10 nucleotides referred to above. The primer extension products are dissociated from their respective templates to produce single stranded molecules, which are treated with the primers above under conditions such that a primer extension product is formed using the single strands produced as templates, resulting in amplification of the target sequences and complementary sequences if present. The conditions allow for the extension of the primer along the control polynucleotide to provide a positive internal control.

Another embodiment of the present invention is a method of producing multiple copies of a target sequence of a target polynucleotide. A combination is provided comprising (1) a single stranded polynucleotide having a sequence that is the target sequence and that is flanked at each end by at least partially complementary first and second flanking sequences, (2) an oligonucleotide primer at least a 10 base portion of which at its 3'-end is hybridizable to that member of the first and second flanking sequences that is at the 3'-end of the single stranded polynucleotide, (3) nucleoside triphosphates, (4) a control polynucleotide, as a template to which at least one of the primers hybridizes except for 1–10 nucleotides at the 3'-end of the primer, and a 3' to 5' exonuclease. Optionally, a modified oligonucleotide primer is included in the above combination. The modified primer is substantially identical to the oligonucleotide primer with the exception of a chemical modification at its 3'-end that prevents degradation, under the reaction conditions, of the 1–10 nucleotides referred to above.

The combination is incubated under conditions for either wholly or partially sequentially or concomitantly (1) dissociating the single stranded polynucleotide from any complementary sequences, (2) hybridizing the oligonucleotide primer with the flanking sequence at the 3'-end of the single stranded polynucleotide and with the control polynucleotide, (3) extending the oligonucleotide primer along the single stranded polynucleotide to provide a first extended polynucleotide primer and degrading the oligonucleotide primer hybridized to the control polynucleotide and extending the degraded oligonucleotide along the control polynucleotide, (4) dissociating the first extended primer and the single stranded polynucleotide and dissociating the control polynucleotide and the extended degraded primer, (5) hybridizing the first extended oligonucleotide primer with the oligonucleotide primer and hybridizing the oligonucleotide primer with the control polynucleotide, (6) extending the oligonucleotide primer along the first extended oligonucleotide primer to provide a second extended polynucleotide primer and degrading the oligonucleotide primer hybridized to the control polynucleotide and extending the oligonucleotide primer along the control polynucleotide to provide an extended degraded primer, (7) dissociating the second extended polynucleotide primer from the first extended polynucleotide primer and the extended degraded primer for the control polynucleotide, and (8) repeating steps (5)–(7) above. The reaction mixture is examined for the presence of extended degraded primer, the presence thereof indicating that the reagents and conditions for producing multiple copies of the target sequence of a target polynucleotide are functional.

Another embodiment of the present invention is a kit comprising in packaged combination (a) an oligonucleotide primer, (b) a control polynucleotide having a sequence to which the oligonucleotide primer hybridizes except for 1–10 nucleotides at the 3'-end of the oligonucleotide primer, (c) a modified oligonucleotide primer that is substantially identical to the oligonucleotide primer except for a chemical modification at its 3'-end that prevents degradation, by a 3' to 5' exonuclease, of the 1–10 nucleotides, (d) nucleoside triphosphates, and (e) a 3' to 5' exonuclease.

DESCRIPTION OF THE SPECIFIC EMBODIMENTS

Figure 1:
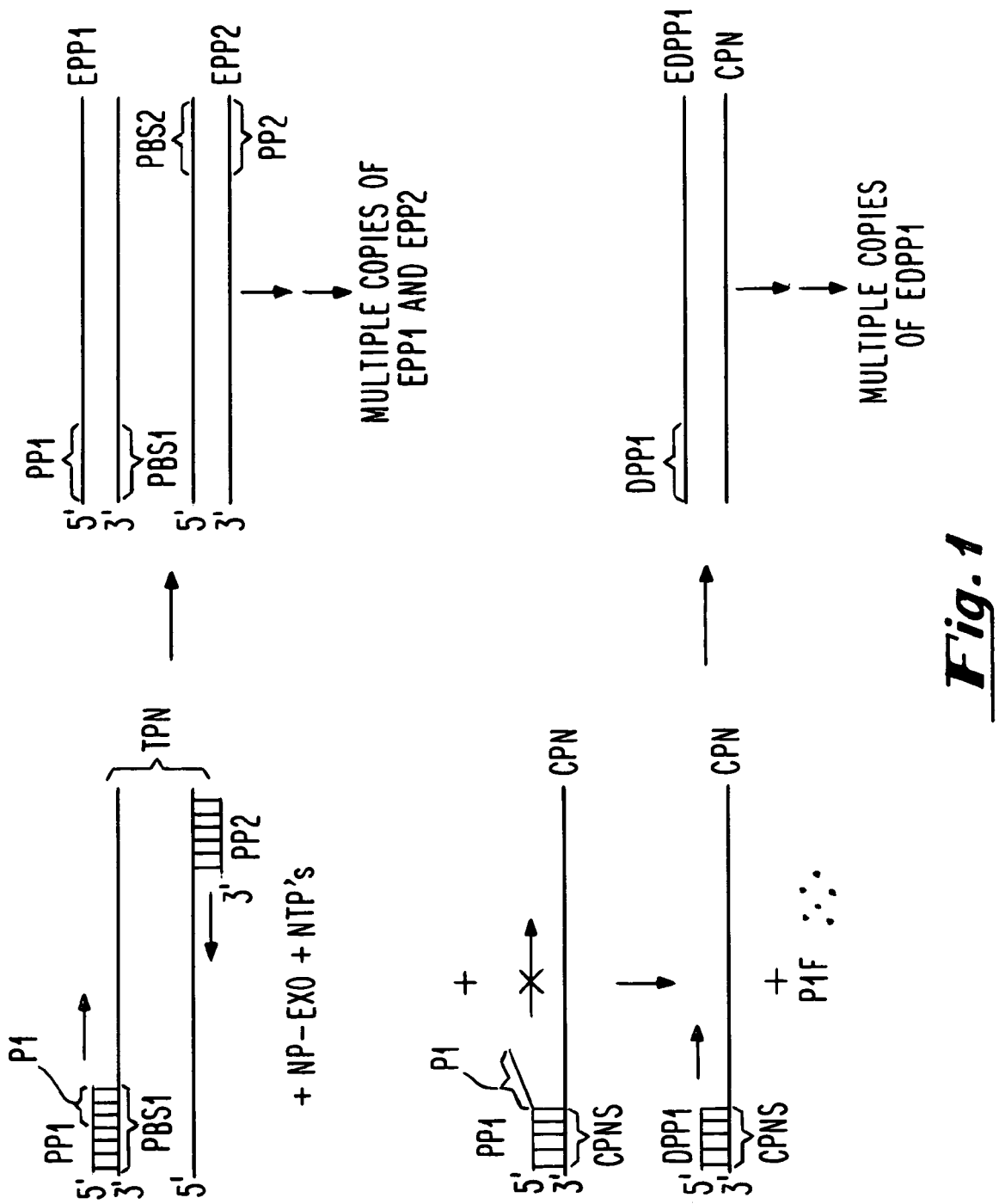
FIGS. 1 and 1A are schematic diagrams depicting certain embodiments in accordance with the present invention.

As mentioned above, in its broadest aspect the present invention permits comparison of the amplification of two or more distinct polynucleotides with respect to their relative detectability during the course of the amplification. The amplification of one polynucleotide is controlled relative to the amplification of another polynucleotide by using a single primer for amplification of both polynucleotides where the primer has a 3'-mismatch with respect to its binding site on one of the polynucleotides. The amount and timing of such regulation is a direct reflection of the concentration of the polynucleotide that does not have a mismatched priming site. Thus, the present invention finds application in the quantitative determination of a polynucleotide in a sample or in the use of internal quantitation controls. For example, when a control polynucleotide is amplified in accordance with the present invention during the amplification of a target polynucleotide, the amount of amplification of the control polynucleotide directly reflects the amount of target polynucleotide. The control polynucleotide can be one that is added to the sample or to the reaction medium or one that is already present in a sample containing the target polynucleotide sequence.

The present invention permits amplification of a positive control polynucleotide template that is controlled by using a primer capable of hybridizing to one of the priming sites of the target polynucleotide and at least one priming site of the control polynucleotide. However, the present invention allows for control of the amplification of the control polynucleotide relative to amplification of the target polynucleotide. This is accomplished by designing the control polynucleotide with a priming site such that the primer has a 3' mismatch in base-pairing to the control polynucleotide but no mismatch to the target polynucleotide. In the presence of a polymerase having 3' to 5' exonuclease activity, the mismatch sequence is degraded whereupon amplification of the control polynucleotide occurs. In this way amplification of the control polynucleotide is controlled so as not to compete directly with that of the target polynucleotide. The control polynucleotide is prevented from consuming so much of the amplification reagents that amplification of target polynucleotide is suppressed. Preferably, suppression of the amplification of the control polynucleotide is controlled by using, in addition to the above oligonucleotide primer, a modified oligonucleotide primer that is substantially the same as the above oligonucleotide primer except for a chemical modification in a portion thereof that prevents degradation of the modified primer when it is hybridized to the control polynucleotide. Accordingly, the amount of primer that supports amplification of the control polynucleotide can be regulated. By controlling the ratio of the oligonucleotide primer and the modified oligonucleotide primer, the level of chain extension of the oligonucleotide primer along the control oligonucleotide can be controlled. The present method improves the performance of both homologous and heterologous controls by reducing the ability of the control to compete with target amplification.

In one aspect the present invention relates to a method for forming multiple copies of a target sequence of a target polynucleotide. The method comprises the step of forming extension products of an oligonucleotide primer at least along the target sequence or along an extended oligonucleotide primer. The extension products are copies of the target sequence. The improvement of the present invention comprises forming the extension products in the presence of a control polynucleotide to which the oligonucleotide primer hybridizes except for the 3'-end of the primer. Under the conditions of the method the oligonucleotide primer is extended along the control polynucleotide in a controlled manner relative to extension of such primer along the target sequence. In this way a positive control is provided because the presence of extended primer corresponding to the control polynucleotide indicates that the reagents and conditions for amplification are functional.

Before proceeding further with a description of the specific embodiments of the present invention, a number of terms will be defined.

Polynucleotide analyte—a compound or composition to be measured that is a polymeric nucleotide, which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological materials by procedures well known in the art. Some examples of such biological materials by way of illustration and not limitation are disclosed in the Table below.

TABLE

| Microorganisms of interest include: | | |
|---|---|---|
| Corynebacteria | | |
| *Corynebacterium diphtheria* | | |
| Pneumococci | | |
| *Diplococcus pneumoniae* | | |
| Streptococci | | |
| *Streptococcus pyrogenes* | | |
| *Streptococcus salivarus* | | |
| Staphylococci | | |
| *Staphylococcus aureus* | | |
| *Staphylococcus albus* | | |
| Neisseria | | |
| *Neisseria meningitidis* | | |
| *Neisseria gonorrhea* | | |
| Enterobacteriaciae | | |
| *Escherichia coil* | | |
| *Aerobacter aerogenes* | The colliform | |
| *Klebsiella pneumoniae* | bacteria | |
| *Salmonella typhosa* | | |
| *Salmonella choleraesuis* | The *Salmonellae* | |
| *Salmonella typhimurium* | | |
| *Shigella dysenteria* | | |
| *Shigella schmitzii* | | |
| *Shigella arabinotarda* | | |
| | The *Shigellae* | |
| *Shigella flexneri* | | |
| *Shigella boydii* | | |
| *Shigella sonnei* | | |
| Other enteric bacilli | | |
| *Proteus vulgaris* | | |
| *Proteus mirabilis* | *Proteus* species | |
| *Proteus morgani* | | |
| *Pseudomonas aeruginosa* | | |
| *Alcaligenes faecalis* | | |
| *Vibrio cholerae* | | |
| Hemophilus-Bordetella group | *Rhizopus oryzae* | |
| *Hemophilus influenza, H. ducryi* | *Rhizopus arrhizua* | |
| Phycomycetes | | |
| *Hemophilus hemophilus* | *Rhizopus nigricans* | |
| *Hemophilus aegypticus* | *Sporotrichum schenkii* | |
| *Hemophilus parainfluenza* | *Flonsecaea pedrosoi* | |
| *Bordetella pertussis* | *Fonsecaea compact* | |
| Pasteurellae | *Fonsecacea dermatidis* | |
| *Pasteurella pestis* | *Cladosporium carrionii* | |
| *Pasteurella tulareusis* | *Phialophora verrucosa* | |
| Brucellae | *Aspergillus nidulans* | |
| *Brucella melitensis* | *Madurella mycetomi* | |
| *Brucella abortus* | *Madurella grisea* | |
| *Brucella suis* | *Allescheria boydii* | |
| Aerobic Spore-forming Bacilli | *Phialophora jeanselmei* | |
| *Bacillus anthracis* | *Microsporum gypseum* | |
| *Bacillus subtilis* | *Trichophyton mentagrophytes* | |
| *Bacillus megaterium* | *Keratinomyces ajelloi* | |
| *Bacillus cereus* | *Microsporum canis* | |
| Anaerobic Spore-forming Bacilli | *Trichophyton rubrum* | |
| *Clostridium botulinum* | *Microsporum adouini* | |
| *Clostridium tetani* | Viruses | |
| *Clostridium perfringens* | Adenoviruses | |
| *Clostridium novyi* | Herpes Viruses | |
| *Clostridium septicum* | Herpes simplex | |
| *Clostridium histolyticum* | Varicella (Chicken pox) | |
| *Clostridium tertium* | Herpes Zoster (Shingles) | |
| *Clostridium bifermentans* | Virus B | |
| *Clostridium sporogenes* | Cytomegalovirus | |
| Mycobacteria | Pox Viruses | |
| *Mycobacterium tuberculosis* | Variola (smallpox) | |
| | hominis | |
| *Mycobacterium bovis* | Vaccinia | |
| *Mycobacterium avium* | Poxvirus bovis | |
| *Mycobacterium leprae* | Paravaccinia | |
| *Mycobacterium paratuberculosis* | *Molluscum contagiosum* | |
| Actinomycetes | Picornaviruses | |
| (fungus-like bacteria) | | |
| *Actinomyces lsaeli* | Poliovirus | |
| *Actinomyces bovis* | Coxsackievirus | |
| *Actinomyces naeslundii* | Echoviruses | |
| *Nocardia asteroides* | Rhinoviruses | |
| *Nocardia brasiliensis* | Myxoviruses | |
| The Spirochetes | Influenza (A, B, and C) | |
| *Treponema pallidum* | Parainfluenza (1–4) | |
| *Spirillum minus* | | |
| *Treponema pertenue* | Mumps Virus | |
| *Streptobacillus monoiliformis* | Newcastle Disease Virus | |
| *Treponema carateum* | Measles Virus | |
| *Borrelia recurrentis* | Rinderpest Virus | |
| *Leptospira icterohemorrhagiae* | Canine Distemper Virus | |
| *Leptospira canicola* | Respiratory Syncytial Virus | |
| Trypanasomes | Rubella Virus | |
| Mycoplasmas | Arboviruses | |
| *Mycoplasma pneumoniae* | | |
| Other pathogens | Eastern Equine Eucephalitis | |
| | Virus | |
| *Listeria monocytogenes* | Western Equine Eucephalitis | |
| | Virus | |
| *Erysipelothrix rhusiopathiae* | Sindbis Virus | |
| *Streptobacillus moniliformis* | Chikugunya Virus | |
| *Donvania granulomatis* | Semliki Forest Virus | |
| *Bartonella bacilliformis* | Mayora Virus | |
| Rickettsiae | St. Louis Encephalitis Virus | |
| (bacteria-like parasites) | | |
| *Rickettsia prowazekii* | California Encephalitis Virus | |
| *Rickettsia mooseri* | Colorado Tick Fever Virus | |
| *Rickettsia rickettsii* | Yellow Fever Virus | |
| *Rickettsia conori* | Dengue Virus | |

TABLE-continued

Microorganisms of interest include:

| | |
|---|---|
| *Rickettsia australis* | Reoviruses |
| *Rickettsia sibiricus* | Reovirus Types 1–3 |
| | Retroviruses |
| *Rickettsia akari* | Human Immunodeficiency Viruses (HIV) |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| | Hepatitis nonA-nonB Virus |
| Chlamydia agents | Tumor Viruses |
| (naming uncertain) | |
| Fungi | Rauscher Leukemia Virus |
| *Cryptococcus neoformans* | Gross Virus |
| *Blastomyces dermatidis* | Maloney Leukemia Virus |
| *Hisoplasma capsulatum* | |
| *Coccidioides immitis* | Human Papilloma Virus |
| *Paracoccidioides brasiliensis* | |
| *Candida albicans* | |
| *Aspergillus fumigatus* | |
| Mucor corymbifer | |
| (*Absidia corymbifera*) | |

Also included are genes, such as hemoglobin gene for sickle-cell anemia, cystic fibrosis gene, oncogenes, cDNA, and the like.

The polynucleotide analyte, where appropriate, may be treated to cleave the analyte to obtain a fragment that contains a target polynucleotide sequence, for example, by shearing or by treatment with a restriction endonuclease or other site specific chemical cleavage method. However, it is an advantage of the present invention that the polynucleotide analyte can be used in its isolated state without further cleavage.

For purposes of this invention, the polynucleotide analyte, or a cleaved fragment obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90–100° C. for a period of about 1 to 10 minutes to produce denatured material.

Amplification of nucleic acids or polynucleotides—any method that results in the formation of one or more copies of a nucleic acid or polynucleotide molecule (exponential amplification) or in the formation of one or more copies of the complement of a nucleic acid or polynucleotide molecule (linear amplification), usually a nucleic acid or polynucleotide analyte, present in a medium.

Exponential amplification of nucleic acids or polynucleotides any method that results in the formation of one or more copies of a nucleic acid or polynucleotide molecule, usually a nucleic acid or polynucleotide analyte, present in a medium. One such method for the enzymatic amplification of specific double stranded sequences of DNA is known as the polymerase chain reaction (PCR), as described above. This in vitro amplification procedure is based on repeated cycles of denaturation, oligonucleotide primer annealing, and primer extension, i.e., "chain extension" of such primer, by thermophilic template dependent polynucleotide polymerase, resulting in the exponential increase in copies, i.e., "chain extension products of the above primers," of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method for amplification is mentioned above and involves amplification of a single stranded polynucleotide using a single polynucleotide primer. The single stranded polynucleotide that is to be amplified contains two non-contiguous sequences that are complementary to one another and, thus, are capable of hybridizing together to form a stem-loop structure. This single stranded polynucleotide may be already part of a polynucleotide analyte or may be created as the result of the presence of a polynucleotide.

Another method for achieving the result of an amplification of nucleic acids is known as the ligase chain reaction (LCR). This method uses a ligase enzyme to join preformed nucleic acid probes. The probes hybridize with the nucleic acid analyte, if present, and ligase is employed to link the probes together resulting in two templates that can serve in the next cycle to reiterate the particular nucleic acid sequence.

Another method for achieving a nucleic acid amplification is the nucleic acid sequence based amplification (NASBA). This method is promoter-directed, enzymatic process that induces in vitro continuous, homogeneous and isothermal amplification of specific nucleic acid.

Another method for amplifying a specific group of nucleic acids is the Q-beta-replicase method, which relies on the ability of Q-beta-replicase to amplify its RNA substrate exponentially.

Linear amplification of nucleic acids or polynucleotides—any method that results in the formation of one or more copies of only the complement of a nucleic acid or polynucleotide molecule, usually a nucleic acid or polynucleotide analyte, present in a medium. Thus, one difference between linear amplification and exponential amplification is that the latter produces copies of the polynucleotide whereas the former produces only the complementary strand of the polynucleotide. In linear amplification the number of complements formed is a constant multiple as opposed to exponential amplification wherein the number of copies is an exponential function.

Target sequence of a target polynucleotide—a sequence of nucleotides to be identified, usually existing within a portion (target polynucleotide) or all of a polynucleotide analyte, the identity of which is known to an extent sufficient to allow preparation of various primers and other molecules necessary for conducting an amplification of the target sequence contained within the target polynucleotide. In general, in primer extension amplification primers hybridize to, and are extended along (chain extended along), at least the target sequence within the target polynucleotide and, thus, the target sequence acts as a template. The extended primers are "chain extension products." The target sequence usually lies between two defined sequences but need not. In general, the primers and other probe polydeoxynucleotides hybridize with the defined sequences or with at least a portion of such target polynucleotide, usually at least a ten nucleotide segment at the 3'-end thereof and preferably at least 15, frequently 20 to 50 nucleotide segment thereof. The target sequence usually contains from about 30 to 5,000 or more nucleotides, preferably 50 to 1,000 nucleotides. The target polynucleotide is frequently a part of the polynucleotide analyte. The target polynucleotide is generally a fraction of a larger molecule or it may be substantially the entire molecule. The minimum number of nucleotides in the target polynucleotide sequence is selected to assure that the presence of target polynucleotide in a sample is a specific indicator of the presence of polynucleotide analyte in a sample. Very roughly, the sequence length is usually greater than about 1.6 log L nucleotides where L is the number of base pairs in the genome of the biologic source of the sample. The maximum number of nucleotides in the target polynucleotide is normally governed by the length of the polynucleotide analyte and its tendency to be broken by shearing, or other processes during isolation and any procedures required to prepare the sample for assay and the efficiency of detection and/or amplification of the sequence.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, preferably, 10 to 50 nucleotides, more preferably, 15 to 25 nucleotides in length.

Various well-known techniques can be employed for preparing oligonucleotides. Such sequences can be obtained by biological synthesis or by chemical synthesis. For short sequences (up to about 100 nucleotides) chemical synthesis is frequently more economical as compared to biological synthesis. For longer sequences standard replication methods employed in molecular biology can be used such as the use of M13 for single stranded DNA as described by J. Messing, *Methods Enzymol* (1983) 101: 20–78.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

Other chemical methods of polynucleotide or oligonucleotide synthesis include phosphotriester and phosphodiester methods (Narang, et al., *Meth. Enzymol* (1979) 68: 90) and synthesis on a support (Beaucage, et al., *Tetrahedron* (1981) *Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

Single stranded polynucleotide having complementary first and second flanking sequences—a sequence of deoxynucleotides normally comprised of at least two segments or flanking sequences that are non-contiguous and complementary with each other. These sequences can hybridize with one another to form a stem-loop structure. It may also contain one or more sequences which, when bound to their complementary sequences, are specific binding sites for receptors such as repressors, restriction enzymes, and the like. The first and second segments or flanking sequences are at the 3'-end and 5'-end, respectively, of the single stranded polynucleotide sequence and each comprises at least ten, preferably at least 15, deoxynucleotides, and/or derivatives thereof. The portion of the single stranded polynucleotide sequence that lies between the flanking sequences comprises the target sequence.

When the single stranded polynucleotide sequence is hybridized with a complementary strand, each end will have a member of a pair of inverted repeats.

End of an oligonucleotide—as used herein this phrase refers to nucleotides, including the terminal nucleotide, at either the 3'- or 5'-opposing sides of an oligonucleotide.

Terminus of an oligonucleotide—as used herein this term refers to the terminal nucleotide at either the 3'- or 5'-end of an oligonucleotide.

Oligonucleotide primer(s)—an oligonucleotide that is usually employed in a chain extension on a polynucleotide template such as in, for example, an amplification of a nucleic acid. The oligonucleotide primer is usually a synthetic deoxynucleotide that is single stranded, containing a sequence at its 3'-end that is capable of hybridizing with a defined sequence of the target polynucleotide. Normally an oligonucleotide primer, and particularly its 3'-end, has at least 50%, preferably 70%, more preferably 90%, most preferably 100%, complementarity to the defined sequence. The number of nucleotides in the hybridizable sequence of a oligonucleotide primer, which hybridizes to a target polynucleotide, should be such that stringency conditions used to hybridize the oligonucleotide primer will prevent excessive random non-specific hybridization. Usually, the number of nucleotides in the oligonucleotide primer will be at least as great as the defined sequence of the target polynucleotide, namely, at least ten nucleotides, preferably at least 15 nucleotides and generally from about 10 to 200, preferably 20 to 50, nucleotides.

Control polynucleotide—a polynucleotide having a sequence that is hybridizable with a portion of an oligonucleotide primer. Accordingly, such a sequence lies in the region involved in initiation of chain extension, i.e., the priming site. Preferably, the control polynucleotide is homologous. The control polynucleotide is usually comprised of a sequence of at least 50 nucleotides, preferably, 100 to 5,000 nucleotides, more preferably, 100 to 500 nucleotides in length. When binding occurs within a control polynucleotide priming site, the effect of binding is such that the oligonucleotide primer, used in chain extension along a target polynucleotide, has a 3' mismatch or non-hybridized portion with respect to the control polynucleotide. In other words, a portion at the 3'-end of the oligonucleotide primer does not hybridize to the control polynucleotide. Thus, the amplification of the control polynucleotide by chain extension of such oligonucleotide primer is reduced relative to the amplification of the target polynucleotide by chain extension of such oligonucleotide primer. Usually, the mismatch results from the oligonucleotide primer having a portion at its 3'-end that does not hybridize with the control polynucleotide. This portion is about 1 to 10, preferably 3 to 5, nucleotides with respect to the priming site of the control polynucleotide. Accordingly, extension of the non-hybridized portion of the 3'-end of the oligonucleotide primer along the control polynucleotide does not occur because the non-hybridized portion of the oligonucleotide primer has no template on which to extend.

Modified oligonucleotide primer—an oligonucleotide primer that is substantially identical, except for a chemical modification at its 3'-end, to the oligonucleotide primer used in the amplification of the target polynucleotide. The modification prevents degradation, by a polymerase having 3' to 5' exonuclease activity, of the 1 to 10 nucleotides of the oligonucleotide primer that do not hybridize to the control polynucleotide. Accordingly, the chemical modification is found within such 1 to 10 nucleotides, usually at or near, within 1 to 5 nucleotides of, the 3'-terminus of the modified oligonucleotide.

Any chemical modification that accomplishes the purposes of the present invention may be utilized. Such modifications include, by way of example and not limitation, phosphorothioates, ethyl phosphonates, carboxamides, sulfonamides, carbamates, acetals and ketals. Furthermore, other modifications will be suggested to those skilled in the art in view of the present disclosure.

Particularly preferred for purposes of the present invention are phosphorothioate modifications. In accordance with the present invention the modified oligonucleotide primer has at its 3'-end, usually within 1 to 5 nucleotides of the 3'-terminus, preferably at the 3'-terminus, a nucleotide monophosphate in which an oxygen of at least one phosphate has been replaced by sulfur. Preferably, an oxygen of 1 to 5 phosphates is replaced by sulfur, more preferably, the oxygen of 1 to 2 phosphates is replaced. The sulfur is frequently bound solely to phosphorus (phosphorothioate group), but can also be bound to a ribose carbon atom or carbon atom of a label. Thus, such modified oligonucleotide primers contain at least one, preferably 1 to 5, more preferably, 1 to 2, phosphorus-sulfur bonds. These sulfur-containing modified oligonucleotide primers can be prepared according to known techniques as described below.

Modified oligonucleotide primers containing at least one monophosphate comprised of a nucleotide monophosphate in which at least one phosphate oxygen is replaced by sulfur can be prepared according to known techniques. Oligonucleotide synthesis can be carried out as described above up to the point where introduction of the phosphorus-sulfur bond is desired. The phosphorus-sulfur bond can be introduced in a number of ways such as, for example, oxidations utilizing a thiolating reagent such as a diacyldisulfide or tetraethyl thiuram disulfide, which are commercially available. The remaining nucleotides are then introduced. Other methods of preparing phosphorothioate containing polynucleotides are described in WO9008838, WO8911486, U.S. Pat. No. 4,910,300, EP318245, the relevant disclosures of which are incorporated herein by reference. Other methods of preparing a phosphorothioate containing polynucleotide are described by (a) Yau, et al., Tetrahedron Lett. (1990)31(14): 1953–1956; (b) Brill, et al., ibid. (1989) 30(48):6621–6624; (c) Caruthers, et al., *Nucleic Acids Symp. Ser.* (1989)21: 119–120; (d) Caruthers, e al., *Nucleosides Nucleotides* (1988)8(5–6): 1011–1014; (e) Brill, et al., *J. Am. Chem. Soc.* (1989)111(6): 2321–2322.

Examples of other chemical modifications at the 3'-end of an oligonucleotide include amide, sulfonamide, thioformal, hydroxylamine, sulfide, ethylene glycol and the like. Such modified oligonucleotides are described, for example, in *Chemical and Engineering News* (1994) 17(No. 16):21–22.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine(A), guanine(G), inosine, and derivatives and analogs thereof. The pyrimidine bases include cytosine (C), thymine (T), uracil (U), and derivatives and analogs thereof. Nucleoside triphosphates include deoxyribonucleoside triphosphates such as dATP, dCTP, dGTP and dTTP and ribonucleoside triphosphates such as rATP, rCTP, rGTP and rUTP. The term "nucleoside triphosphates" also includes derivatives and analogs thereof, which are exemplified by those derivatives that are recognized and polymerized in a similar manner to the underivitized nucleoside triphosphates. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like. The term "nucleoside triphosphate" includes the derivatives and analogs thereof.

Nucleotide—a base-sugar-phosphate combination that is the monomeric unit of nucleic acid polymers, i.e., DNA and RNA.

Modified nucleotide—is the unit in a nucleic acid polymer that results from the incorporation of a modified nucleoside triphosphate during an amplification reaction and therefore becoming part of the nucleic acid polymer.

Nucleoside—is a base-sugar combination or a nucleotide lacking a phosphate moiety.

Nucleotide polymerase—a catalyst, usually an enzyme, for forming an extension of an oligonucleotide along a DNA template where the extension is complementary thereto. The nucleotide polymerase is a template dependent polynucleotide polymerase and utilizes nucleoside triphosphates as building blocks for extending the 3'-end of a oligonucleotide to provide a sequence complementary with the single stranded portion of the polynucleotide to which the oligonucleotide is hybridized to form a duplex. Usually, the catalysts are enzymes, such as DNA polymerases.

3' to 5' exonuclease—for purposes of the present invention an enzyme is considered to be a 3' to 5' exonuclease, or to have 3' to 5' exonuclease activity, when, under the conditions of the reactions contemplated herein, it acts as a sequence-independent enzyme that catalyzes the selective cleavage of unhybridized nucleotides from the 3'-end of an oligonucleotide primer when a portion of such primer is hybridized to the control polynucleotide and may also act as a nucleotide polymerase (in the latter sense it may be considered as a polymerase comprising a 3' to 5' exonuclease). The enzyme selectively cleaves the unhybridized nucleotides of the oligonucleotide primer to the point at which there are no unhybridized nucleotides at the 3'-terminus of the portion of the oligonucleotide primer hybridized to the control polynucleotide but does not cleave the hybridized portion or the control polynucleotide. The 3' to 5'-nucleases useful in the present invention must be stable under the conditions used in the present method and are usually thermally stable nucleotide polymerases. Such enzymes may be derived from any source such as cells, bacteria, such as *E. coli*, plants, animals, virus, thermophilic bacteria, and so forth wherein the polymerase may be modified chemically or through genetic engineering to provide for thermal stability and/or increased activity. Such enzymes include Pfu DNA polymerase (native and recombinant) from Stratagene, La Jolla, Calif., Ultma DNA polymerase from Perkin Elmer, Foster City, Calif., r Bst DNA polymerase from Epicentre Technologies, Madison, Wis., VENT DNA polymerase from New England Biolabs, Beverly, Mass., Tli DNA polymerase from Promega Corp., Madison, Wis., and Pwo DNA polymerase from Boehringer Mannheim, Indianapolis, Ind., and the like.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by, elevating the temperature, increasing the ratio of cosolvents, lowering the salt concentration, and the like.

Homologous or substantially identical—In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Non-contiguous—sequences are non-contiguous, there being at least one, usually at least 10, nucleotides present in the target polynucleotide sequence between the two segments or between two sequences, S1 and S2, of a polynucleotide.

Contiguous—sequences are considered to be contiguous when there are no nucleotides between two segments or between two sequences of a polynucleotide.

Copy of a sequence—a sequence that is a direct identical copy of a single stranded polynucleotide sequence as differentiated from a sequence that is complementary to the sequence of such single stranded polynucleotide.

Means for extending a primer—a nucleotide polymerase or a single stranded template polynucleotide having a sequence other than at its 3' end that can hybridize to at least the 3' end of the primer or both. Means for extending a primer also includes nucleoside triphosphates or analogs thereof capable of acting as substrates for the enzyme and other materials and conditions required for enzyme activity such as a divalent metal ion (usually magnesium), pH, ionic strength, organic solvent (such as formamide), and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA—DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label or reporter group or reporter molecule—a member of the signal producing system. Usually the label or reporter group or molecule is conjugated to or becomes bound to a polynucleotide probe or an oligonucleotide primer and is capable of being detected directly or, through a specific binding reaction, and can produce a detectable signal. Labels include a polynucleotide primer or specific polynucleotide sequence that can provide a template for amplification or ligation or act as a ligand such as for a repressor protein. Preferably, an oligonucleotide primer will have, or be capable of having, a label. In general, any label that is detectable can be used. The label can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal Producing System—The signal producing system may have one or more components, at least one component being the label or reporter group. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. The signal-producing system is described more fully in the U.S. Pat. No. 5,595,891, the relevant disclosure of which is incorporated herein by reference.

Ancillary Materials—Various ancillary materials will frequently be employed in the methods and assays carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

As mentioned above, one aspect of the present invention provides an improvement in nucleic acid amplification reactions by providing for a positive control. Accordingly, the present invention avoids false negatives in such amplification reactions. The methods generally involve the step of forming extension products of an oligonucleotide primer at least along the target sequence or along an extended oligonucleotide primer. The extension products are copies of the target sequence. The improvement of the present invention comprises forming the extension products in the presence of a control polynucleotide to which the oligonucleotide primer hybridizes except for 1–10 nucleotides at the 3'-end of the primer. Under the conditions of the method the oligonucleotide primer is extended along the control polynucleotide in a controlled manner relative to the extension of the oligonucleotide primer along the target sequence. Optionally, a modified oligonucleotide primer is included in the above combination. The modified primer is substantially identical to the oligonucleotide primer with the exception of a chemical modification at its 3'-end that prevents degradation, under the reaction conditions, of the 1–10 nucleotides referred to above. In this approach the level of chain extension of the oligonucleotide primer along the control oligonucleotide can be controlled by controlling the ratio of the oligonucleotide primer and the modified oligonucleotide primer.

One embodiment of the present invention is depicted in FIG. 1. In this embodiment an amplification by PCR is chosen by way of example and not limitation. The sample suspected of containing the nucleic acid or target polynucleotide (TPN), being double stranded and having a target sequence to be amplified by PCR, is combined with two different polynucleotide primers (PP1 and PP2), a nucleotide polymerase having 3' to 5' exonuclease activity (NP-EXO), nucleoside triphosphates (NTP's) and a control polynucleotide (CPN). CPN has at its 3'-end a sequence CPNS that can hybridize with PP1 except for a portion (P1) of 1–10 nucleotides at the 3'-end of PP1.

Conditions are chosen to achieve thermal cycling of the reaction mixture. Under such conditions PP1 hybridizes with primer binding site PBS1 of TPN if TPN is present and with CPNS of CPN and primer PP2 hybridizes with primer binding site PBS2 of TPN. Extension of PP1 and PP2 along the respective strands of TPN, respectively, yields extended PP1 (EPP1) and extended PP2 (EPP2), which are each complements of the respective strands of TPN. Molecules EPP1 and EPP2 serve as templates for primers PP2 and PP1, respectively. Continued thermal cycling thus leads to amplification of the target sequence.

In addition, PP1 hybridizes, except for portion P1, to CPN at binding site CPNS. Accordingly, PP1 hybridized to CPN has a portion P1 at the 3'-end of PP1 that does not hybridize to CPN. Therefore, the 3'-end of PP1 cannot undergo chain extension along CPN until P1 is degraded to fragments P1F by the exonuclease activity of NP-EXO so that the 3'-end of PP1 is fully hybridized to CPN. Thus, during thermal cycling the extension of molecules of degraded PP(PP1 minus P1 (or DPP1)) along CPN is controlled relative to the extension of PP1 along TPN because of the delay due to the degradation of P1 from PP1. The amplification of the control is slowed in relation to the amplification of the target sequence. Thus, the presence of a control does not lead to consumption of so much of the reagents that amplification of the target polynucleotide sequence is suppressed. In this manner an effective positive control is achieved.

Figure 1A:
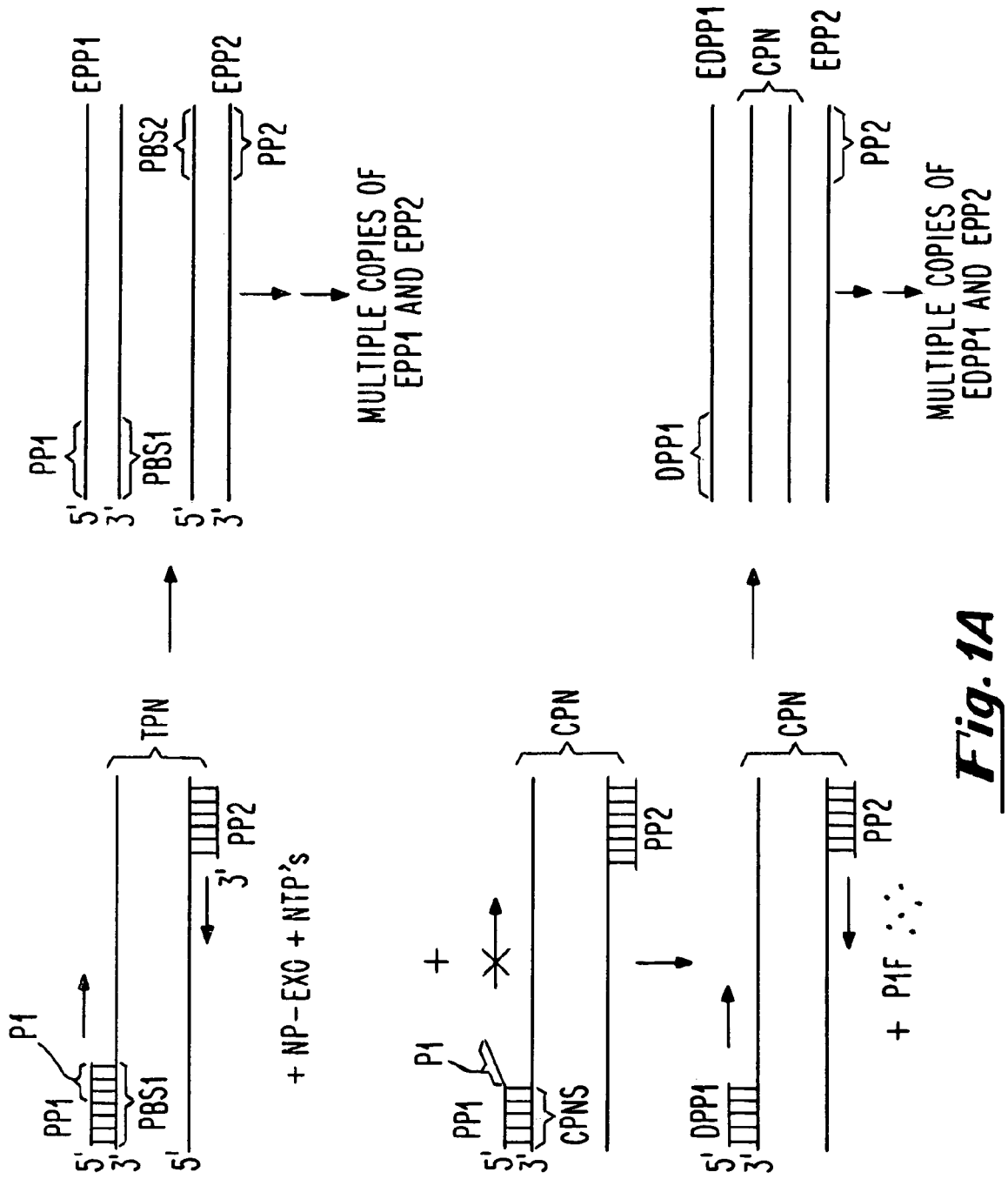

The control polynucleotide can be an oligonucleotide that is unrelated to the target polynucleotide sequence except for the portion to which PP1 binds. On the other hand, the control polynucleotide can correspond to one of the strands of the target polynucleotide sequence except for the portion of the control polynucleotide to which the 3'-end of primer PP1 does not bind. The control polynucleotide can be double stranded. In this situation, where there is correspondence between the control polynucleotide and the target polynucleotide sequence, a second primer, e.g., PP2 above, would also bind to and be extended along the strand other than that to which PP1 binds (see FIG. 1A).

A 3'-end mismatch between PP2 and the strand of the control polynucleotide to which it binds would result in control of the extension of PP2 along such strand and furtherance of the positive control desired.

As mentioned above CPN functions as a control polynucleotide as follows. When TPN is present in the sample, PP1 hybridizes with both TPN and CPN. However, the extension of PP1 along CPN is controlled relative to its extension along TPN because degradation of portion P1 that must occur before PP1 can extend along CPN. The extension of PP1 along TPN is not dependent on the prior degradation of PP1 as is the case for its extension along CPN. The number of copies and complements of CPN resulting from the hybridization of PP1 with, and extension along, CPN to give extension products that are copies of and complements of CPN is diminished when TPN is present in the sample. When TPN is not present in the sample, the extension of PP1 proceeds along. CPN and many more copies and complements of CPN are formed because there is no competing reaction involving the extension of PP1 along TPN.

Another way in which the extension of PP1 along CPN can be controlled is by adjusting the concentration of PP1 and/or CPN or of PP1 and PP2.

Figure 2:
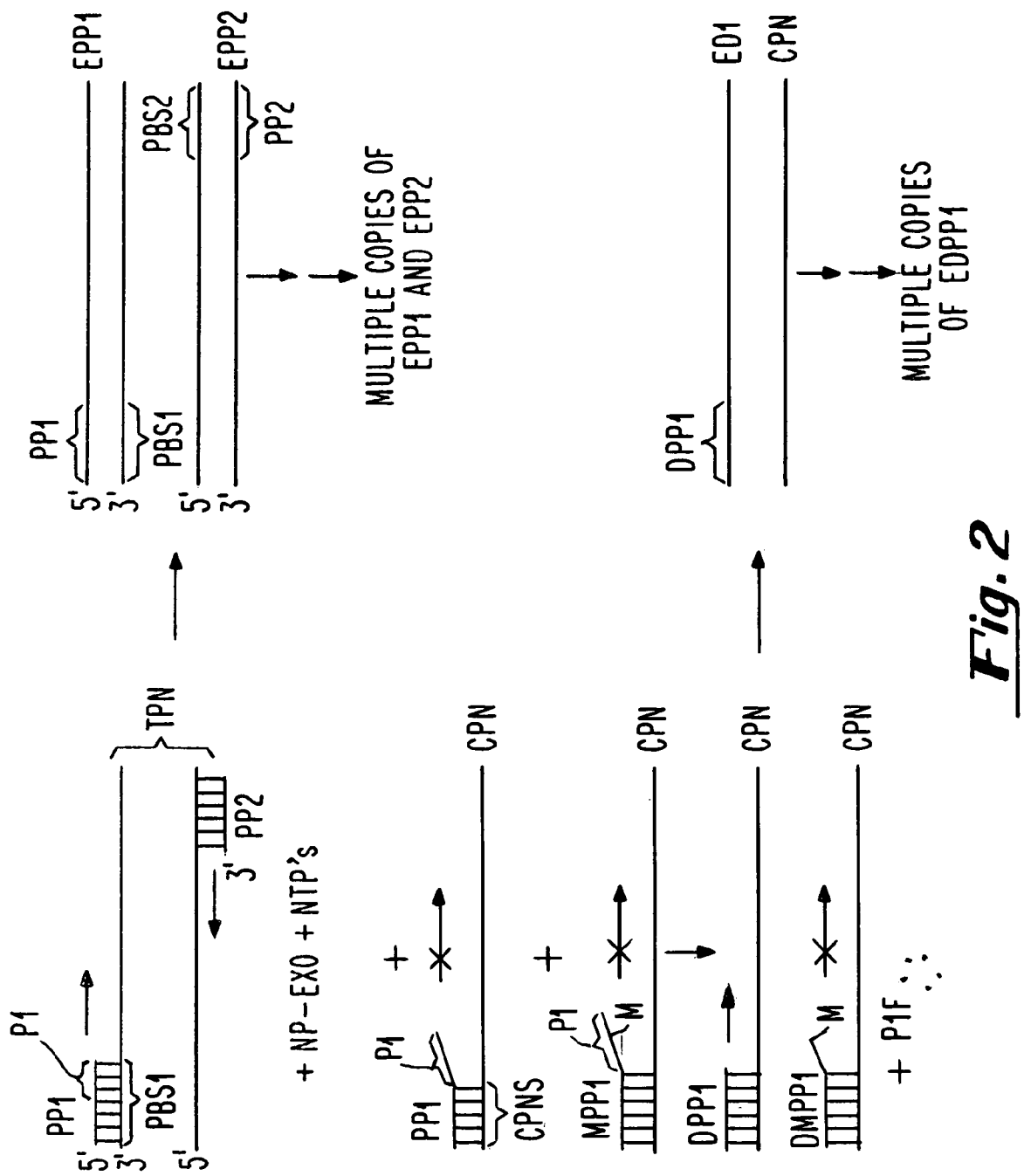
FIG. 2 is a schematic diagram depicting an alternate embodiment in accordance with the present invention.

Another embodiment in accordance with the present invention is set forth in FIG. 2. In this embodiment an additional primer MPP1 is employed that is a modified oligonucleotide primer as defined above. As mentioned above, MPP1 corresponds to PP1 but contains within P1 a modification that renders P1 undegradable or resistant to degradation when PP1 is hybridized to CPN. The sample suspected of containing the nucleic acid or target polynucleotide (TPN), being double stranded and having a target sequence (TPNS) to be amplified by PCR, is combined with three polynucleotide primers (PP1, MPP1 and PP2), a nucleotide polymerase preferably having 3' to 5' exonuclease activity (NP-EXO), nucleoside triphosphates (NTP's) and a control polynucleotide (CPN). CPN has at its 3'-end a sequence CPNS that can hybridize with PP1 and MPP1 except for a portion (P1) of 1–10 nucleotides at the 3'-end of PP1 and MPP1.

Conditions are chosen to achieve thermal cycling of the reaction mixture. Under such conditions PP1 and MPP1, respectively, hybridize with primer binding site PBS1 of TPN if TPN is present and with CPNS of CPN and primer PP2 hybridizes with primer binding site PBS2 of TPN. Extension of PP1, MPP1 and PP2 along the respective strands of TPN, respectively, yields extended PP1 and MPP1 (EPP1 and EMPP1, respectively) and extended PP2 (EPP2), which are each complements of the respective strands of TPN (EPP1 and EMPP1). Continued thermal cycling thus leads to amplification of the target sequence. Molecules EPP1 and EMPP1, on the one hand, and EPP2, on the other hand, serve as templates for primers PP2, on the one hand, and PP1 and MPP1, on the other hand.

In addition, as mentioned above, PP1 and MPP1 hybridize, except for portion P1, to CPN at binding site CPNS. Accordingly, PP1 and MPP1 hybridized to CPN have portion P1 at the 3'-end of PP1 and MPP1, respectively, that does not hybridize to CPN. Therefore, the 3'- end of PP1 cannot chain extend along CPN until P1 is degraded to fragments P1F by the exonuclease activity of the enzyme so that the 3'-end of PP1 is fully hybridized to CPN. Furthermore, since MPP1 has modification M, it is degraded only until the modification is encountered. Usually, the modification is within 1 to 10 nucleotides, preferably, 1 to 4 nucleotides, from the point where MPP1 is hybridized to CPNS. Accordingly, since MPP1 still contains a portion P2 that is not hybridized to CPN, MPP1 cannot chain extend along CPN. Thus, during thermal cycling the extension of molecules of PP1 minus P1 along CPN occurs more slowly than the extension of PP1 along TPN because of the delay due to the degradation of P1 from PP1 and because of the competing hybridization of MPP1 to CPN. The amplification of the control polynucleotide is slowed in relation to the amplification of the target sequence. Thus, the presence of a control polynucleotide does not lead to consumption of so much of the reagents that amplification of the target polynucleotide sequence is suppressed. In this manner an effective positive control is achieved.

In the above embodiment the amount of primer that supports amplification of the control polynucleotide can be regulated by the amount of unmodified primer PP1. This permits a relatively sensitive way in which the amount of amplified control polynucleotide obtained can be controlled. In general, the ratio of modified primer to unmodified primer is about 5:1 to 1:1, preferably about 2.5:1. Since both PP1 and MPP1 bind to, and are extended along, the target polynucleotide sequence TPN, no decrease in target sensitivity should be reflected by incorporation of the modified oligonucleotide primer into the amplification reaction.

Figure 3:
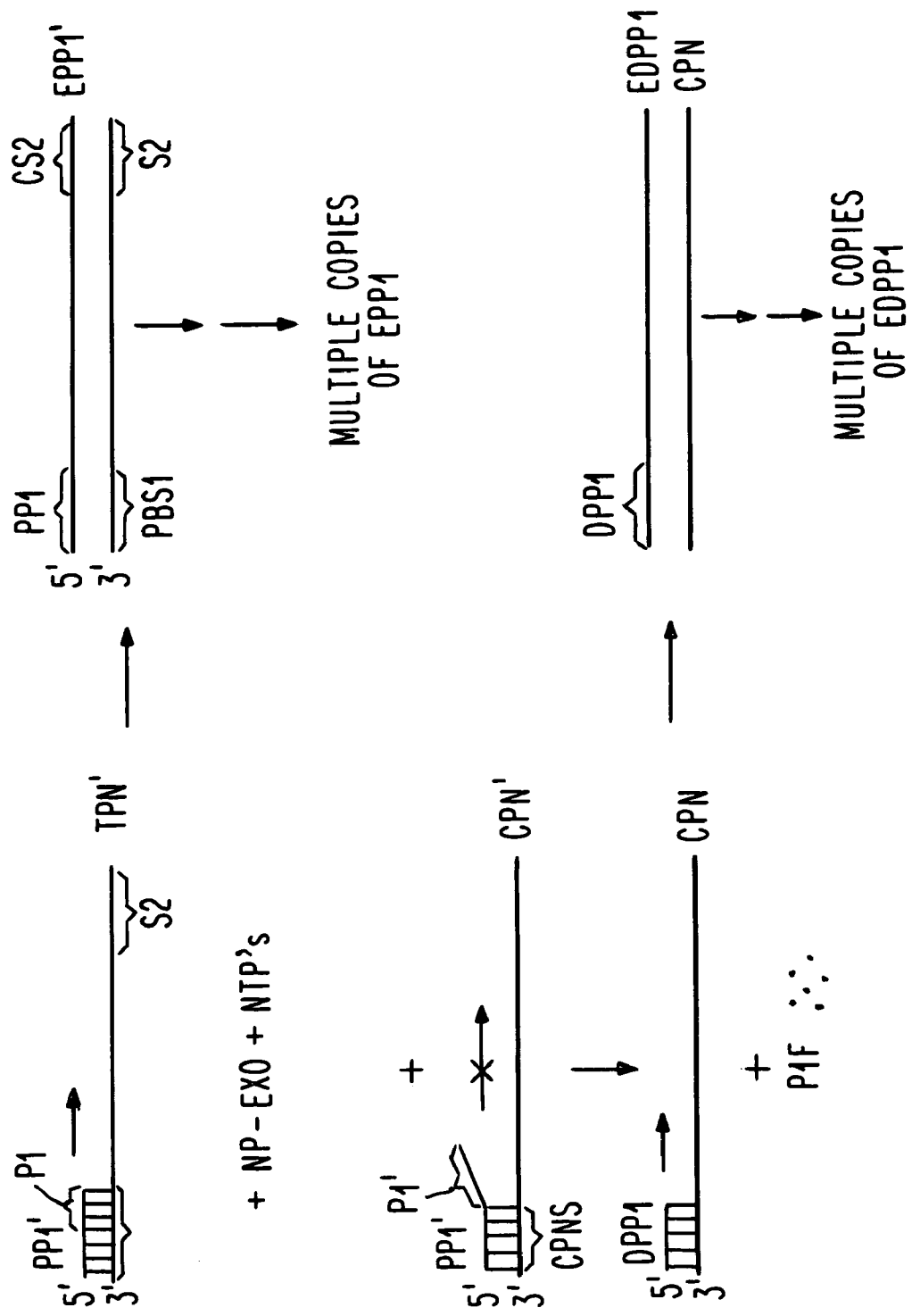
FIG. 3 is a schematic diagram depicting an alternate embodiment in accordance with the present invention.

Another embodiment of the present invention is depicted in FIG. 3. In this embodiment an amplification by single primer amplification is chosen by way of example and not limitation. The target polynucleotide TPN' is a single stranded polynucleotide that has an inverted repeat, i.e., sequence PBNS1' of TPN' is complementary to sequence S2 of TPN'. The sample suspected of containing TPN' is combined with a single oligonucleotide primer PP1', a nucleotide polymerase preferably having 3' to 5' exonuclease activity NP-EXO, nucleoside triphosphates (NTP's) and a control polynucleotide (CPN'). CPN' has at its 3'-end a sequence CPNS' that can hybridize with PP1' except for a portion (P1') of 1–10 nucleotides at the 3'-end of PP1'.

Conditions are chosen to achieve thermal cycling of the reaction mixture. Under such conditions PP1' hybridizes with primer binding site PBS1' of TPN' if TPN' is present and with CPNS' of CPN'. Extension of PP1' along the respective strands of TPN' yields extended PP1' (EPP1'), which is a complement of TPN'. Since S2 is the complement of PBNS', EPP1' contains sequence CS2 that is the complement of S2 and of PP1', which can now bind to and be extended along both TPN' and EPP1'. Continued thermal cycling thus leads to amplification of the target sequence. Molecule EPP1' serves as a template for primer PP1'.

In addition, PP1' hybridizes, except for portion P1', to CPN' at binding site CPNS'. Accordingly, PP1' hybridized to CPN' has a portion P1' at the 3'-end of PP1' that does not hybridize to CPN'. Therefore, the 3'-end of PP1' cannot chain extend along CPN' until P1' is degraded to fragments P1F' by the exonuclease activity of NP-EXO so that the 3'-end of PP1' is fully hybridized to CPN'. Thus, during thermal cycling the extension of molecules of PP1' minus P1' (DPP1') along CPN' is controlled relative to the extension of PP1' along TPN' because of the delay due to the degradation of P1' from PP1'. The amplification of the control is slowed in relation to the amplification of the target sequence. Thus, the presence of a control does not lead to consumption of so much of the reagents that amplification of the target polynucleotide sequence is suppressed. In this manner an effective positive control is achieved. It should be apparent that the above embodiment can also employ a modified oligonucleotide primer as described above.

The present method has application where the target polynucleotide sequence is DNA or RNA. In one aspect of the invention one or more of the reagents, such as, for example, an oligonucleotide primer, is labeled with a label (reporter molecule). The reporter molecule can be, for example, a detectable group or a binder such as biotin or a nucleotide sequence other than the sequence that hybridizes with the target sequences. The extended primer(s) can be detected by means of a reporter molecule covalently bonded to a probe. The probe has a nucleotide sequence that is homologous or complementary to a portion of the target nucleotide sequence other than those sequences to which the primers bind.

Another embodiment of the invention concerns a method for detecting the presence of a polynucleotide analyte in a sample suspected of containing the polynucleotide analyte. A medium containing the sample is treated as described above to yield a target polynucleotide from the polynucleotide analyte, if present, or the polynucleotide analyte itself is the target polynucleotide. The medium is then combined with reagents for conducting an amplification, which depend on the particular amplification protocol chosen. The target polynucleotide is then subjected to an embodiment of the above method in accordance with the present invention to generate multiple copies of the target polynucleotide sequence, which are then detected. An examination is conducted for the presence of the extended primer, the presence thereof indicating the presence of the polynucleotide analyte. The amplification is carried out until a sufficient number of molecules of extended primer are obtained to provide an accurate detection of the polynucleotide analyte. Depending on the amplification protocol chosen, the number of cycles are at least three, preferably, at least 10; usually it is preferable that the number of cycles be less than 30. Where the polynucleotide analyte is RNA, the nucleotide polymerase comprises a reverse transcriptase.

In carrying out the methods in accordance with the present invention, including amplification, an aqueous medium is employed. Other polar cosolvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to 9.5, more usually in the range of about 5.5–8.5, and preferably in the range of about 6–8. The pH and temperature are chosen and varied, as the case may be, so as to cause, either simultaneously or sequentially, dissociation of any internally hybridized sequences, hybridization of the primers and any other probes with the target polynucleotide sequence, hybridization of the polydeoxynucleotide primer with target polynucleotide sequences, extension of the primer(s), and dissociation of the extended primer(s). In some instances, a compromise is made in optimizing the speed, efficiency, and specificity of these steps depending on whether it is desired to perform the above steps sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the methods. Normally, in conducting the methods the medium is cycled between two or three temperatures. The temperatures for the methods generally range from about 10 to 105° C., more usually from about 40 to 99° C., preferably 50 to 98° C. The exact temperatures can be varied depending on the salt concentration, pH, solvents used, length of and composition of the target polynucleotide sequence and the primer. Relatively low temperatures of from about 30 to 65° C. can be employed for the extension steps, while denaturation and hybridization can be carried out at a temperature of from about 50 to 105° C.

Where the present method is utilized in single primer amplification or in PCR, the method is conducted for a time sufficient to achieve a desired number of copies of the extended primer or a sequence complementary thereto. This, in turn, depends on the purpose for which the amplification is conducted, such as, for example, an assay for a polynucleotide analyte. Generally, the time period for conducting the method will be from about 1 to 10 minutes per cycle and any number of cycles can be used from 1 to as high as 200 or more, usually 5 to 80, frequently 10–60. As a matter of convenience it is usually desirable to minimize the time period and the number of cycles. In general, the time period for a given degree of amplification can be shortened, for example, by selecting concentrations of nucleoside triphosphates sufficient to saturate the polynucleotide polymerase and by increasing the concentrations of polynucleotide polymerase and polynucleotide primer. Generally, the time period for conducting the method will be from about 5 to 200 minutes. As a matter of convenience, it will usually be desirable to minimize the time period.

The concentration of the enzyme having 3' to 5' exonuclease activity is sufficient to realize the requisite level of delay of the extension of the primer along the control polynucleotide, usually about 0.1 to 10 units per one hundred microliter reaction volume, preferably, 1 to 5 units per one hundred microliter reaction volume. Where such enzyme also functions as a polymerase, the concentration of this polymerase will be chosen to be sufficient to accomplish chain extension. The concentration of the polymerase is usually determined empirically. Preferably, a concentration is used that is sufficient such that further increase in the concentration does not decrease the time for the amplification by over 5-fold, preferably 2-fold. The primary limiting factor generally is the cost of the reagent.

The amount of the target polynucleotide which is to be copied can be as low as one or two molecules in a sample but generally may vary from about $10^2$ to $10^{10}$, more usually from about $10^3$ to $10^8$ molecules in a sample preferably at least $10^{-21}$M in the sample and may be $10^{-10}$ to $10^{-19}$M, more usually $10^{-14}$ to $10^{-19}$M.

The amount of the control polynucleotide is usually less than that of the target polynucleotide, generally, about ten fold to ten thousand fold less than the target polynucleotide. In the case of a polynucleotide primer with an exonuclease resistant 3'-end, the control polynucleotide can be in excess of the target polynucleotide, but, generally not more than a ten thousand fold excess in relation to the amount or concentration of the target polynucleotide.

The amount of the oligonucleotide primer(s) will be at least as great as the number of copies desired and will usually be $1\times10^{-10}$ to $1\times10^{-6}$ moles per sample, where the sample is 1–1,000 mL. Usually, the primer(s) are present in at least 0.1 µM, preferably 0.5 µM, and more preferably at least about 1 µM. Preferably, the concentration of the oligonucleotide primer(s) is substantially in excess over, preferably at least $1\times10^{14}$ times greater than, the concentration of the target polynucleotide sequence.

The concentration of the deoxynucleoside triphosphates in the medium can vary widely; preferably, these reagents are present in an excess amount. The deoxynucleoside triphosphates are usually present at $10^{-6}$ to $10^{-2}$ M, preferably $10^{-5}$ to $10^{-3}$M.

The order of combining of the various reagents to form the combination may vary. Generally, the target polynucleotide sequence is obtained from a sample containing such sequence or a polynucleotide analyte that has been treated to obtain such sequence. Generally, the target polynucleotide sequence is combined with a pre-prepared combination of deoxynucleoside triphosphates and template-dependent polydeoxynucleotide polymerase. The oligonucleotide primer(s) may be included in the prepared combination or may be added subsequently. However, simultaneous addition of all of the above, as well as other step-wise or sequential orders of addition, may be employed.

The concentration and order of addition of reagents and conditions for the method are governed generally by the desire to maximize the number of copies of the extended primer(s) and the rate at which such copies are formed and the fidelity of replication. Generally, it is desirable to increase the number of copies of the extended primer by at least a factor of 102, preferably a factor of $10^4$, more preferably 1 or more.

In carrying out the method of the invention as applied to the detection of a polynucleotide analyte, the considerations as to media, pH, temperature, and times can be as described above.

While the concentrations of the various reagents are generally determined by the concentration range of interest of the polynucleotide analyte, the final concentration of many of the reagents is normally determined empirically to optimize the sensitivity of the assay over the range of interest. The concentration of the other reagents in an assay generally is determined following the same principles as set forth above. The primary consideration is that a sufficient number of copies of extended primer(s) be produced in relation to the polynucleotide analyte sequence so that such copies can be readily detected and provide an accurate determination of the polynucleotide analyte.

The copies of extended primer(s) can be detected in numerous ways. For example, in the present method, molecules of the oligonucleotide primer can be labeled with a reporter molecule such as a ligand, a small organic molecule, a polynucleotide sequence, a protein, support, a member of an operator-repressor pair, intercalation dye and the like. Any standard method for specifically detecting nucleic acid sequences can be used.

One method for detecting nucleic acids is to employ nucleic acid probes. One method utilizing probes is described in U.S. patent application Ser. No. 773,386, filed Sep. 6, 1985, the disclosure of which is incorporated herein by reference.

Other assay formats and detection for in U.S. patent applications Ser. Nos. 07/229,252 (abandoned) and 07/399,795 filed Jan. 19, 1989, and Aug. 29, 1989, respectively, U.S. Pat. No. 5,595,891, U.S. Pat. No. 5,439,793 and U.S. patent application Ser. No. 07/776,538 (abandoned) filed Oct. 11, 1991, which have been incorporated herein by reference.

Examples of particular labels or reporter molecules and their detection can be found in U.S. Pat. No. 5,595,891, the relevant disclosure of which is incorporated herein by reference.

Detection of the signal will depend upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

Another embodiment of the present invention relates to the quantitative determination of a target polynucleotide in a sample suspected of containing the target polynucleotide. It is known that, when PCR amplifications, for example, are followed during the course of amplification, the earliest time of detection of an amplifying DNA species or amplicon can often be directly related to the amount of target DNA that is present in the sample. This technology is made more reliable by adding a known concentration of a control DNA to the same reaction mix containing an unknown target concentration. The earliest time of detection of these two amplicons can be compared and used to determine the concentration of the unknown target. The added control DNA thereby serves as an internal concentration control for the unknown target.

The above method is limited in that the control concentration of DNA cannot be more than 100 to 1000 times more or less concentrated than the unknown target. If the concentrations of the two DNA's in the reaction containers are outside this range, then, the highest concentration DNA amplifies before the lower concentration DNA can amplify. The lower concentration DNA is then never detected, and a comparison of the two DNA's, control and target, cannot be accomplished. Since the concentration of the target DNA can, in some applications, vary more than 1000 fold, the practical result is that several reactions need to be run in separate reaction containers with varying control DNA concentration to be certain that the unknown target concentration falls within 100–1000 fold of the control DNA concentration.

In accordance with the present invention a control polynucleotide, as that term is used in the present invention, is introduced into the amplification reaction mixtures as a reference polynucleotide at a concentration such that the control polynucleotide always amplifies to a detectable level, but never amplifies so much that it obscures or eliminates the signal of the target amplification. Accordingly, the range of concentrations in which a single reaction container reliably identifies the concentration of the target polynucleotide is extended.

As a matter of convenience, predetermined amounts of reagents employed in the present invention can be provided in a kit in packaged combination. A kit can comprise in packaged combination (a) an oligonucleotide primer, (b) a control polynucleotide having a sequence to which the oligonucleotide primer hybridizes except for 1–10 nucleotides at the 3'-end of the oligonucleotide primer, (c) a modified oligonucleotide primer that is substantially identical to the oligonucleotide primer except for a chemical modification at its 3'-end that prevents degradation, by a 3' to 5' exonuclease, of the 1 to 10 nucleotides, (d) nucleoside triphosphates, and (e) a nucleotide polymerase, which may or may not have exonuclease activity. In the event that the nucleotide polymerase does not have 3' to 5' exonuclease activity, then the kit further comprises an enzyme having 3' to 5' exonuclease activity.

A kit for amplification of a target polynucleotide sequence comprises the above items and for conducting PCR would include in addition a second polynucleotide primer, where the primers are related in that a product of the extension of one along said target sequence serves as a template for the extension of the other.

In assaying for a polynucleotide analyte in a sample, a kit useful in the present method can comprise, in packaged combination with other reagents mentioned above, reagents for forming a target polynucleotide sequence from a polynucleotide analyte. Furthermore, the oligonucleotide primer can be labeled or can be provided with groups to render the sequence labeled or bound to a support. The kit can further include a labeled polynucleotide probe capable of binding to an amplified target polynucleotide sequence. The kit can further include members of a signal producing system and also various buffered media, some of which may contain one or more of the above reagents.

The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kit can further include a written description of a method in accordance with the present invention as described above.

EXAMPLES

The invention is demonstrated further by the following illustrative examples. Temperatures are in degrees centigrade (° C.) and parts and percentages are by weight, unless otherwise indicated.

The following terms are defined:
HPLC—high performance liquid chromatography.
DTT—dithiothreitol
min—minute
sec—second
hr—hour The oligonucleotides used in the examples below were synthesized on a Biosearch 8750 DNA synthesizer by standard phosphoroamidite methods. After deprotection with ammonium hydroxide, the oligonucleotides were purified by HPLC.

Example 1

In this example two oligonucleotides plus one oligonucleotide with 3' phosphorothioate additions on the 3' end were used for the PCR amplification. The phosphorothioate additions are indicated with an in the oligonucleotide sequence.

Primer A-5'CGACTCACTATAGGGCGAATTGGGC3' (SEQ ID NO. 1).
Primer B-5'CGACTCACTATAGGGCGMTTGG*G*C3' (SEQ ID NO. 2).
Primer C-5'CATTAGGCACCCCAGGCTTTACAC3' (SEQ ID NO. 3).

The target polynucleotide was plasmid pGem5 from Promega Company, Madison, Wis. The control polynucleotide was plasmid pGem3 also from Promega Company. pGem3 has a 57 nucleotide smaller multiple cloning site (MCS) than pGem5. The primers were designed to the MCS's of these plasmids. Primer A was designed to the upstream region of the MCS of pGem5 where the plasmid sequence differentiates from pGem3. Primer A is completely complementary to pGem5 and also complementary to pGem 3 except for the last four nucleotides at the 3' end. Primer C, the downstream primer, is complementary to both pGem3 and 5 and serves as the downstream primer in all PCR amplifications. The amplification products generated by primer A and primer C were 212 nucleotides and nucleotides for pGem3 and -Gem5, respectively, and were easily differentiated by agarose gel electrophoresis.

PCR was performed with the heat-stable cloned Pfu DNA polymerase having 3;-exonuclease activity (Stratagene, La Jolla, Calif.). The final composition of the PCR mix was 10 mM Tris-HCl (pH 8.8) 50 mM KCl, 1.5 mM $MgCl_2$, 0.1% TRITON®X-100 (polyoxyethylene (10) isooctylphenyl ether), 7.5 mM DTT, 0.2 mM DT of each nucleoside triphosphate and 5 units of cloned Pfu polymerase. The final primer concentration was 1.0 µM. pGem3 and pGem5 were diluted in deionized distilled water prior to use to a concentration of 1 microgram per microliter. The relevant DNA sample was added to the individual sample last. All titration reactions were carried out with a common master mix. Cycling parameters were an initial 5 min denaturation at 95° C. followed by 45 cycles of 60° C. for 1 min, extension at 72° C. for 1 min, and denaturation at 94° C. for 30 sec. Total PCR reaction volume of 100 µL was used in an Ericomp water-cooled thermocycler (Ericomp, Inc., San Diego, Calif.). The two plasmids, pGem3 and pGem5, were titrated in amplification reactions at 10 and $10^6$ target molecules per amplification reaction in an effort to determine the level of amplification control and competition between the two templates.

After amplification the reactions were analyzed on agarose gels prepared from ultra-pure agarose from Bethesda Research Laboratories (Gaithersburg, Md.) at a concentration of 2.0%. Ethidium bromide was added for visualization under ultra-violet light at a concentration of 0.5 mg/ml. One-third of each reaction, combined with a 6× loading dye (0.25% bromophenol blue, 0.25% xylene cyanol, and 15% ficoll in water), was loaded in every agarose gel lane and visualized by UV irradiation.

Results:

Amplification of target polynucleotide pGem5 occurred at a higher level than that for the control polynucleotide pGem3 in amplification reactions where the target polynucleotide was at equal or greater concentrations.

Table 1 compares the different amplification frequencies at various concentrations of control and target polynucleotides. The data indicated that an exonuclease digestion of primer A was reflected in the control polynucleotide usually being amplified to a lesser extent than a like concentration of target polynucleotide (see Table 1). When the concentration of the control polynucleotide was higher than that of the target polynucleotide, the delay caused by the 3' to 5' exonuclease digestion was overcome and the control polynucleotide was amplified at an equal or greater level than the target polynucleotide. In this particular example the enchanced level of amplification of target polynucleotide decreases as the concentration of control polynucleotide increases.

TABLE 1

AMPLIFICATION REACTIONS WITH PRIMERS A AND C
Number of Copies of Target

| Number of copies of control templates | $10^6$ | $10^5$ | $10^4$ | $10^3$ | $10^2$ |
|---|---|---|---|---|---|
| $10^6$ | ++/+ | ++/+ | −/++ | −/++ | −/+++ |
| $10^5$ | +++/+ | ++/+ | +/++ | (+)/++ | −/++ |
| $10^4$ | ++/− | ++/− | ++/− | +/+ | +/+ |
| $10^3$ | +++/− | +++/− | ++/− | +/+ | +/+ |
| $10^2$ | +++/− | +++/− | +++/− | ++/++ | +++/++ |

$\dfrac{\text{Target}}{\text{Control}}$

Regulation of primer A exonuclease digestion was a means of controlling the rate of amplification of the control polynucleotide during the amplification of both target polynucleotide and control polynucleotide.

Coamplification of both target polynucleotide and control polynucleotide at both low and high target polynucleotide concentrations was more successful with the incorporation of the phosphorothioate substituted primer B (Table 2). Amplification reactions were carried out with ratios of 2.5:1 (Table 2) and 5:1 (not shown) of phosphorothiolated primer (primer B) to non-phosphorothiolated primer (primer A). Amplification of both the target polynucleotide and the control polynucleotide was observed with $10^5$ to $10^6$ copies of the control polynucleotide over a wide range of concentrations of target polynucleotide (100–1,000,000 target polynucleotide molecules).

TABLE 2

AMPLIFICATION REACTIONS WITH PRIMERS A, B AND C
Number of Copies of Target

| Number of copies of control templates | $10^6$ | $10^5$ | $10^4$ | $10^3$ | $10^2$ |
|---|---|---|---|---|---|
| $10^6$ | +++ / + | ++ / + | ++ / ++ | + / ++ | + / ++ |
| $10^5$ | +++ / + | +++ / + | ++ / + | + / + | (+) / ++ |
| $10^4$ | +++ / − | +++ / + | ++ / + | ++ / + | ++ / ++ |
| $10^3$ | +++ / − | +++ / − | +++ / − | ++ / + | + / + |
| $10^2$ | +++ / − | +++ / − | +++ / − | ++ / − | ++ / − |

Target / Control

Amplification of the same mixture without the use of primer A (primers B and C only) produced only the target amplicon with no detectable amount of the amplicon from the control polynucleotide. When Pfu polymerase lacking 3' to 5' exonuclease activity was used to catalyze amplification in the presence of all three primers, again only the target polynucleotide was amplified.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the following claims.

---

What is claimed is:

1. In a method for forming multiple copies of a target sequence of a target polynucleotide, said method comprising the steps of combining a sample with reagents for forming said multiple copies, subjecting said sample to polynucleotide amplification conditions sufficient to form the multiple copies if the target sequence is present in said sample, said reagent comprising an oligonucleotide primer and polymerase; and forming an extension product of the oligonucleotide primer at least along said target sequence, said extension product being a complement of said target sequence, the improvement which comprises forming said extension product in the presence of a control polynucleotide to which said oligonucleotide primer hybridizes except for a 3'-mismatch on said oligonucleotide primer, under polynucleotide amplification conditions wherein the extension of said oligonucleotide primer along said control polynucleotide is controlled by the 3'-mismatch relative to the extension of said oligonucleotide primer along said target sequence.

2. The method of claim 1, wherein the extension of said oligonucleotide primer along said control polynucleotide is controlled by contacting the 3'-mismatch with a 3' to 5' exonuclease.

3. The method of claim 2, wherein the extension of said oligonucleotide primer along said control polynucleotide is controlled by digesting the 3'-mismatch with the 3' to 5' exonuclease and extending the oligonucleotide primer along the control polynucleotide under the polynucleotide amplification conditions.

4. The method of claim 1, wherein the method further comprises adding to the combination of reagents and sample a modified oligonucleotide primer that hybridizes to the target sequence and the second polynucleotide under the polynucleotide amplification conditions, the modified oligonucleotide primer comprising a chemical modification at its 3'-end that prevents digestion by a 3' to 5' exonuclease.

5. The method of claim 1, wherein the target sequence is single-stranded and said invert repeat structures that hybridize to the oligonucleotide primer under the polynucleotide amplification conditions.

6. The method of claim 1, wherein the target sequence is double-stranded and said inverted repeat structures form a stem-loop that hybridizes to the oligonucleotide primer under the polynucleotide amplification conditions.

7. The method of claim 1, wherein the amount of the second polynucleotide is about ten fold to about ten thousand fold less than the target polynucleotide.

8. In a method for amplifying a target sequence of a target polynucleotide, said method comprising combining a sample suspected of containing said target polynucleotide with reagents for amplifying said target sequence if present and subjecting said combination to polynucleotide amplification conditions wherein said target sequence if present is amplified, said reagents comprising primer A and primer B and a polymerase having 3' to 5' exonuclease activity, the improvement which comprises (a) including in said combination a control polynucleotide, to which said primer A hybridizes except for 1–10 nucleotides at the 3-end of said primer, wherein said primer extends along said target sequence and extends along said control polynucleotide to produce copies of said control polynucleotide only after said 1 to 10 nucleotides are degraded by said polymerase having said 3' to 5' exonuclease activity and (b) detecting the presence of said copies of said control polynucleotide, the presence thereof indicating that said reagents and polynucleotide amplification conditions for amplifying said target sequence are functional.

9. The method of claim 8 wherein said oligonucleotide primer is fully complementary to that portion of said target sequence to which it hybridizes and is complementary to that portion of said control polynucleotide to which it hybridizes except for said 1 to 10 nucleotides at the 3'-end thereof.

10. The method of claim 8 wherein a modified oligonucleotide primer is included in said combination where said modified oligonucleotide primer is substantially identical to said oligonucleotide primer except for a chemical modification at its 3'-end that prevents degradation, by said 3' to 5' exonuclease, of said 1 to 10 nucleotides.

11. The method of claim 10 wherein said chemical modification is selected from the group consisting of phosphorothioates, ethyl phosphonates, carboxamides, sulfonamides, carbamates, acetals and ketals.

12. The method of claim 10 wherein said chemical modification is a phosphorothioate.

13. The method of claim 8 wherein said oligonucleotide primer hybridizes to said control polynucleotide except for 3–5 nucleotides at the 3'-end of said oligonucleotide primer.

14. The method of claim 8 wherein the presence of amplified target sequence is detected and related to the presence of said target polynucleotide.

15. In a method for forming multiple copies of a target sequence of a single stranded target polynucleotide ("target sequence"), said method comprising:

(a) hybridizing to the 3'-end of said target sequence a first oligonucleotide primer ("first primer"), (b) extending, in the presence of a polymerase having 3' to 5' exonuclease activity, said first primer along at least said target sequence, said first primer being capable of hybridizing to, and being extended along, (1) said extended first primer or (2) an extended second oligonucleotide primer ("second primer") wherein said extended second primer results from the extension of a second primer capable of hybridizing to and extending along a polynucleotide that is complementary (complementary polynucleotide) to said target sequence, (c) dissociating said extended first primer from said target sequence, (d) hybridizing, to the 3-end of said extended first primer, said first or said second primer, (e) extending said first or said second primer along said extended first primer, (f) dissociating said extended first primer or said extended second primer from said extended first primer, (g) hybridizing, to the 3'-end of said extended first or second primer, said first primer, and (h) repeating steps (e)–(g), the improvement comprising
  (i) including, as a positive internal control in the same reaction mixture subjected to steps (a)–(g) above, a control polynucleotide, to which said first or second primer hybridizes except for 1–10 nucleotides at the 3'-end of said first or said second primer, wherein said first or said second primer extends along said control polynucleotide to produce copies of said control polynucleotide only after said 1–10 nucleotides are degraded by said polymerase having 3' to 5' exonuclease activity and (ii) detecting said copies of said control polynucleotide, wherein steps (a)–(h) are performed under polynucleotide amplification conditions.

16. The method of claim 15 wherein said first primer is fully complementary to that portion of said target sequence to which it hybridizes and is complementary to that portion of said control polynucleotide to which it hybridizes except for said 1 to 10 nucleotides at the 3'-end thereof.

17. The method of claim 15 wherein a modified oligonucleotide primer is included in said combination wherein said modified oligonucleotide primer is identical to said first or said second primer except for a chemical modification at its 3'-end that prevents degradation by said 3' to 5' exonuclease, of said 1 to 10 nucleotides.

18. The method of claim 17 wherein said chemical modification is selected from the group consisting of phosphorothioates, ethyl phosphonates, carboxamides, sulfonamides, carbamates, acetals and ketals.

19. The method of claim 17 wherein said chemical modification is a phosphorothioate.

20. The method of claim 15 wherein said first or said second primer hybridizes to said control polynucleotide except for 3–5 nucleotides at the 3'-end of said first or said second primer.

21. The method of claim 15 wherein the presence of said extended first primer and/or said extended second primer is detected and related to the presence of said target polynucleotide.

22. The method of claim 15 wherein said control polynucleotide is 50 to 5000 nucleotides in length.

23. The method of claim 15 wherein said control polynucleotide is present in the reaction mixture at a concentration of from about 1 pM to 100 pM.

24. The method of claim 15 wherein the repeating of steps (e)–(g) is achieved by repeated temperature cycling.

25. The method of claim 24 wherein temperature cycling is repeated at least 3 times.

26. The method of claim 15 wherein said target polynucleotide is DNA.

27. The method of claim 15 wherein said extending is carried out in the presence of nucleoside triphosphates.

28. The method of claim 15 wherein said control polynucleotide contains at least a 15 nucleotide sequence that is not in the target sequence.

29. The method of claim 15 wherein said first and said second primers are different and said control polynucleotide contains a sequence at its 5'-end that is identical to the sequence at the 5'-end of said second primer.

30. The method of claim 9 wherein said first and said second primers are different and said extended first primer is a template for said second primer and said extended second primer is a template for said first primer.

31. A method for forming multiple copies of at least one double stranded polynucleotide ("polynucleotide") said polynucleotide comprising a single stranded target polynucleotide sequence ("target sequence") and its complementary sequence ("complementary sequence"), said method comprising:

(a) treating a sample suspected of containing one or more of said double stranded polynucleotides with (i) at least two oligonucleotide primers capable of hybridizing to a portion of each target sequence and its complementary sequence suspected of being present in said sample under polynucleotide amplification conditions for hybridizing said primers to and extending said primers along said target sequence and said complementary sequences, wherein said primers are selected such that the extension product formed from one primer ("primer A"), when it is dissociated from its complement, can serve as the template for the extension product of another primer ("primer B"), (ii) a control polynucleotide, as a template to which a control Primer hybridizes except for 1–10 nucleotides of the primer at the 3'-end, wherein said control primer is selected from the group consisting of primer A and primer B, and (iii) a 3' to 5' exonuclease wherein said primers extend, respectively, along said target sequence and said complementary sequence and the control primer extends along said control polynucleotide only after said 1–10 nucleotides are degraded by said 3' to 5' exonuclease, (b) dissociating primer extension products from their respective templates to produce single stranded molecules and (c) treating the single stranded molecules produced in step (b) with the primers of step (a) under polynucleotide amplification conditions such that a primer extension product is formed using the single strands produced in step (b) as templates, resulting in amplification of the target sequences and complementary sequences if present, said polynucleotide amplification conditions allowing for the extension of the control primer along said control polynucleotide to provide said positive internal control.

32. The method of claim 31 wherein said primer A or primer B is fully complementary to that portion of said target sequence to which it hybridizes and is complementary to that portion of said control polynucleotide to which it hybridizes except for said 1 to 10 nucleotides at the 3'-end thereof.

33. The method of claim 31 wherein a modified oligonucleotide primer is included in said combination wherein said modified oligonucleotide primer is identical to said one of said primers except for a chemical modification at its 3'-end that prevents degradation, by said 3'–5' exonuclease, of said 1 to 10 nucleotides.

34. The method of claim 33 wherein said chemical modification is selected from the group consisting of phosphorothioates, ethyl phosphonates, carboxamides, sulfonamides, carbamates, acetals and ketals.

35. The method of claim 33 wherein said chemical modification is a phosphorothioate.

36. The method of claim 31 wherein said primer A or primer B hybridizes to said control polynucleotide except for 3–5 nucleotides at the 3'-end thereof.

37. The method of claim 31 wherein the presence of primer extension products is detected and related to the presence of said target polynucleotide.

38. The method of claim 31 wherein said control polynucleotide is 50 to 5000 nucleotides in length.

39. The method of claim 31 wherein said control polynucleotide is present in the
reaction mixture at a concentration of from about 1 µM to 100 µM.

40. The method of claim 31 wherein the repeating of steps (a)–(c) is achieved by repeated temperature cycling.

41. The method of claim 40 wherein temperature cycling is repeated at least 3 times.

42. The method of claim 31 wherein said target polynucleotide is DNA.

43. The method of claim 31 wherein said extending is carried out in the presence of nucleoside triphosphates.

44. The method of claim 31 comprising adding to the product of step (c) a labeled oligonucleotide probe for each sequence being amplified capable of hybridizing to said sequence or a mutation thereof and determining whether said hybridization has occurred.

45. A method of producing multiple copies of a target sequence of a target polynucleotide, which comprises:
   (a) providing in combination (1) a single stranded polynucleotide having a sequence that is said target sequence and that is flanked at each end by at least partially complementary first and second flanking sequences, (2) an oligonucleotide primer at least a 10 base portion of which at its 3'-end is hybridizable to that member of said first and second flanking sequences that is at the 3'-end of said single stranded polynucleotide, (3) nucleoside triphosphates, (4) a control polynucleotide, as a template to which said oligonucleotide primer hybridizes except for 1–10 nucleotides at the 3'-end of said nucleotide primer, and (5) a 3' to 5' exonuclease wherein said primer extends along said target sequence and said primer extends along said control polynucleotide only after said 1–10 nucleotides are degraded by said 3' to 5' exonuclease,
   (b) incubating said combination under polynucleotide amplification conditions for (1) dissociating said single stranded polynucleotide from any complementary sequences, (2) hybridizing said oligonucleotide primer with the flanking sequence at the 3'-end of said single stranded polynucleotide and with said control polynucleotide, (3) extending said oligonucleotide primer along said single stranded polynucleotide to provide a first extended oligonucleotide primer and degrading said oligonucleotide primer hybridized to said control polynucleotide and extending said degraded oligonucleotide along said control polynucleotide, (4) dissociating said first extended primer and said single stranded polynucleotide and dissociating said control polynucleotide and said extended degraded primer, (5) hybridizing said first extended oligonucleotide primer with said oligonucleotide primer and hybridizing said oligonucleotide primer and said control polynucleotide, (6) extending said oligonucleotide primer along said first extended oligonucleotide primer to provide a second extended oligonucleotide primer and degrading said oligonucleotide primer hybridized to said control polynucleotide and extending said oligonucleotide primer along said control polynucleotide to provide an extended degraded primer, (7) dissociating said second extended oligonucleotide primer from said first extended oligonucleotide primer and said extended degraded primer from said control polynucleotide, and (8) repeating steps (5)–(7) above, and
   (c) detecting the presence of said extended degraded primer, the presence thereof indicating that said reagents and polynucleotide amplification conditions for producing multiple copies of said target sequence of a target polynucleotide are functional.

46. The method of claim 45 wherein said oligonucleotide primer is fully complementary to that portion of said target sequence to which it hybridizes and is complementary to that portion of said control polynucleotide to which it hybridizes except for said 1 to 10 nucleotides at the 3'-end thereof.

47. The method of claim 45 wherein a modified oligonucleotide primer is identical to said oligonucleotide primer except for a chemical modification at its 3'-end that prevents degradation, by said 3'–5' exonuclease, of said 1 to 10 nucleotides.

48. The method of claim 47 wherein said chemical modification is selected from the group consisting of phosphorothioates, ethyl phosphonates, carboxamides, sulfonamides, carbamates, acetals and ketals.

49. The method of claim 47 wherein said chemical modification is a phosphorothioate.

50. The method of claim 45 wherein said oligonucleotide primer hybridizes to said control polynucleotide except for 3–5 nucleotides at the 3'-end thereof.

51. The method of claim 45 wherein the presence of extended oligonucleotide primer is detected and related to the presence of said target polynucleotide.

52. The method of claim 45 wherein said control polynucleotide is 50 to 5000 nucleotides in length.

53. The method of claim 45 wherein said control polynucleotide is present in the reaction mixture at a concentration of about 1 pM to 100 pM.

54. The method of claim 45 wherein the repeating of steps (5)–(7) is achieved by repeated temperature cycling.

55. The method of claim 54 wherein temperature cycling is repeated at least 3 times.

56. The method of claim 45 wherein said target polynucleotide is DNA.

57. The method of claim 45 comprising adding to the product of step (c) a labeled oligonucleotide probe capable of hybridizing to said sequence or a mutation thereof and determining whether said hybridization has occurred.

58. The method of claim 45 wherein said oligonucleotide primer is labeled with a reporter group.

* * * * *